US010178959B1

(12) United States Patent
Homyk et al.

(10) Patent No.: US 10,178,959 B1
(45) Date of Patent: Jan. 15, 2019

(54) NON-INVASIVE FLOW MONITORING

(71) Applicant: Verily Life Sciences LLC, Mountian View, CA (US)

(72) Inventors: Andrew Homyk, Belmont, CA (US); Russell Norman Mirov, Los Altos, CA (US)

(73) Assignee: Verily Life Sciences LLC, Mountain View, CA (US)

(*) Notice: Subject to any disclaimer, the term of this patent is extended or adjusted under 35 U.S.C. 154(b) by 461 days.

(21) Appl. No.: 14/327,764

(22) Filed: Jul. 10, 2014

(51) Int. Cl.
A61B 5/026 (2006.01)
A61B 5/00 (2006.01)
A61B 5/024 (2006.01)

(52) U.S. Cl.
CPC ............ *A61B 5/0261* (2013.01); *A61B 5/681* (2013.01); *A61B 5/6824* (2013.01); *A61B 5/0002* (2013.01); *A61B 5/02438* (2013.01); *A61B 5/02444* (2013.01)

(58) Field of Classification Search
CPC ..... A61B 5/0261; A61B 5/681; A61B 5/6824; A61B 5/02438; A61B 5/02444; A61B 5/0002
See application file for complete search history.

(56) References Cited

U.S. PATENT DOCUMENTS

| 4,608,993 | A | * | 9/1986 | Albert | A61B 8/065 600/457 |
| 4,862,894 | A | * | 9/1989 | Fujii | A61B 5/0064 600/479 |
| 5,163,437 | A | * | 11/1992 | Fujii | A61B 3/1233 600/476 |
| 5,240,006 | A | * | 8/1993 | Fujii | A61B 3/1233 351/221 |

(Continued)

FOREIGN PATENT DOCUMENTS

WO 2013/030744 A1 3/2013
WO WO 2015150199 A1 * 10/2015 ........... A61B 5/6898

OTHER PUBLICATIONS

Briers, David J. "Laser Speckle Contrast Imaging for Measuring Blood Flow." Optica Applicata, vol. XXXVII, No. 1-2, 2007.*
(Continued)

*Primary Examiner* — Angela M Hoffa
(74) *Attorney, Agent, or Firm* — McDonnell Boehnen Hulbert & Berghoff LLP

(57) ABSTRACT

Systems are provided for detecting the flow of blood in vasculature by illuminating the blood with a source of coherent illumination and detecting one or more time-varying properties of a light speckle pattern that results from the scattering of the coherent illumination by tissue and blood. The movement of blood cells and other light-scattering elements in the blood causes transient, short-duration changes in the speckle pattern. High-frequency sampling or
(Continued)

other high-bandwidth processing of a detected intensity at one or more points in the speckle pattern could be used to determine the flow of blood in the vasculature. Such flow-measuring systems are also presented as wearable devices that can be operated to detect the flow in vasculature of a wearer. Systems and methods provided herein can additionally be applied to measure flow in other scattering fluid media, for example in a scattering industrial, medical, pharmaceutical, or environmental fluid.

12 Claims, 12 Drawing Sheets

(56) References Cited

U.S. PATENT DOCUMENTS

| | | | |
|---|---|---|---|
| 6,220,686 B1* | 4/2001 | Ludi | B41J 11/008 347/4 |
| 6,944,494 B2* | 9/2005 | Forrester | A61B 1/042 600/478 |
| 7,231,243 B2* | 6/2007 | Tearney | A61B 1/00082 600/407 |
| 7,737,947 B2* | 6/2010 | Schroeder | G06F 3/0317 345/166 |
| 7,925,056 B2* | 4/2011 | Presura | A61B 5/02444 356/28 |
| 8,032,200 B2* | 10/2011 | Tearney | A61B 1/00082 600/407 |
| 8,089,465 B2* | 1/2012 | Lutian | G06F 3/0317 250/221 |
| 8,217,897 B2* | 7/2012 | Lutian | G06F 3/0317 250/221 |
| 8,920,332 B2* | 12/2014 | Hong | A61B 5/02427 600/309 |
| 8,935,119 B2* | 1/2015 | Yuen | G01B 21/16 702/138 |
| 8,945,017 B2* | 2/2015 | Venkatraman | A61B 5/721 600/500 |
| 8,948,832 B2* | 2/2015 | Hong | A61B 5/02427 600/301 |
| 8,954,135 B2* | 2/2015 | Yuen | H04W 4/027 600/407 |
| 8,956,303 B2* | 2/2015 | Hong | A61B 5/02427 600/310 |
| 8,965,730 B2* | 2/2015 | Yuen | A61B 5/00 702/141 |
| 8,998,815 B2* | 4/2015 | Venkatraman | A61B 5/721 600/481 |
| 9,005,129 B2* | 4/2015 | Venkatraman | A61B 5/721 600/301 |
| 9,014,790 B2* | 4/2015 | Richards | A61B 5/02438 600/473 |
| 9,044,149 B2* | 6/2015 | Richards | A61B 5/02427 |
| 9,044,171 B2* | 6/2015 | Venkatraman | A61B 5/0002 |
| 9,079,060 B2* | 7/2015 | Hong | A61B 5/00 |
| 9,113,794 B2* | 8/2015 | Hong | A61B 5/02427 |
| 9,113,795 B2* | 8/2015 | Hong | A61B 5/02427 |
| 9,168,419 B2* | 10/2015 | Hong | A61B 5/4812 |
| 9,198,604 B2* | 12/2015 | Venkatraman | A61B 5/0002 |
| 9,226,673 B2* | 1/2016 | Ferguson, Jr. | A61B 5/0059 |
| 9,237,855 B2* | 1/2016 | Hong | A61B 5/02427 |
| 9,241,635 B2* | 1/2016 | Yuen | A61B 5/02405 |
| 9,271,658 B2* | 3/2016 | Ferguson, Jr. | A61B 5/0059 |
| 9,282,902 B2* | 3/2016 | Richards | A61B 5/02427 |
| 9,282,931 B2* | 3/2016 | Tearney | A61B 1/00082 |
| 9,307,917 B2* | 4/2016 | Hong | A61B 5/02427 |
| 9,402,552 B2* | 8/2016 | Richards | A61B 5/02427 |
| 9,410,979 B2* | 8/2016 | Yuen | G01P 7/00 |
| 9,456,787 B2* | 10/2016 | Venkatraman | A61B 5/721 |
| 2006/0253007 A1* | 11/2006 | Cheng | A61B 5/0048 600/310 |
| 2008/0146952 A1* | 6/2008 | Presura | A61B 5/02444 600/508 |
| 2009/0209871 A1* | 8/2009 | Ueki | A61B 5/0261 600/504 |
| 2012/0065490 A1 | 3/2012 | Zharov et al. | |
| 2013/0184544 A1 | 7/2013 | Su et al. | |
| 2013/0324866 A1 | 12/2013 | Gladshtein | |
| 2014/0094663 A1 | 4/2014 | LeBoeuf et al. | |
| 2014/0107493 A1* | 4/2014 | Yuen | H04W 4/027 600/473 |
| 2014/0125491 A1* | 5/2014 | Park | H04W 4/027 340/870.01 |
| 2014/0127996 A1* | 5/2014 | Park | H04W 4/027 455/41.1 |
| 2014/0135612 A1* | 5/2014 | Yuen | A61B 5/02405 600/407 |
| 2014/0200423 A1* | 7/2014 | Eisen | A61B 5/14551 600/340 |
| 2014/0206954 A1* | 7/2014 | Yuen | A61B 5/02405 600/301 |
| 2014/0266939 A1* | 9/2014 | Baringer | H01Q 21/28 343/729 |
| 2014/0273858 A1* | 9/2014 | Panther | A61B 5/0002 455/41.2 |
| 2014/0275850 A1* | 9/2014 | Venkatraman | A61B 5/0002 600/301 |
| 2014/0275852 A1* | 9/2014 | Hong | A61B 5/02427 600/301 |
| 2014/0275854 A1* | 9/2014 | Venkatraman | A61B 5/721 600/301 |
| 2014/0276119 A1* | 9/2014 | Venkatraman | A61B 5/721 600/479 |
| 2014/0278220 A1* | 9/2014 | Yuen | G01B 21/16 702/150 |
| 2014/0278229 A1* | 9/2014 | Hong | A61B 5/7455 702/160 |
| 2014/0288390 A1* | 9/2014 | Hong | A61B 5/02427 600/301 |
| 2014/0288391 A1* | 9/2014 | Hong | A61B 5/02427 600/301 |
| 2014/0288392 A1* | 9/2014 | Hong | A61B 5/02427 600/301 |
| 2014/0288435 A1* | 9/2014 | Richards | A61B 5/02427 600/479 |
| 2014/0288436 A1* | 9/2014 | Venkatraman | A61B 5/721 600/479 |
| 2014/0288438 A1* | 9/2014 | Venkatraman | A61B 5/721 600/483 |
| 2014/0297217 A1* | 10/2014 | Yuen | G01B 21/16 702/138 |
| 2014/0297218 A1* | 10/2014 | Yuen | G01B 21/16 702/141 |
| 2014/0305204 A1* | 10/2014 | Hong | A61B 5/7455 73/504.08 |
| 2014/0316305 A1* | 10/2014 | Venkatraman | A61B 5/1112 600/595 |
| 2014/0358012 A1* | 12/2014 | Richards | A61B 5/02438 600/479 |
| 2015/0025393 A1* | 1/2015 | Hong | A61B 5/02427 600/479 |
| 2015/0025394 A1* | 1/2015 | Hong | A61B 5/02427 600/479 |
| 2015/0122018 A1* | 5/2015 | Yuen | G01B 21/16 73/384 |
| 2015/0173631 A1* | 6/2015 | Richards | A61B 5/02427 600/479 |
| 2015/0196256 A1* | 7/2015 | Venkatraman | A61B 5/721 600/301 |
| 2015/0201853 A1* | 7/2015 | Hong | A61B 5/02427 600/301 |
| 2015/0201854 A1* | 7/2015 | Hong | A61B 5/02427 600/301 |
| 2015/0223708 A1* | 8/2015 | Richards | A61B 5/02427 600/479 |
| 2015/0230735 A1* | 8/2015 | Venkatraman | A61B 5/1112 600/301 |
| 2015/0314166 A1* | 11/2015 | Hong | A61B 5/7455 702/151 |

(56) References Cited

U.S. PATENT DOCUMENTS

| | | | | |
|---|---|---|---|---|
| 2016/0007925 A1* | 1/2016 | Mirov | ............... | A61B 5/0059 356/400 |
| 2016/0036118 A1* | 2/2016 | Baringer | ............... | H01Q 21/28 343/702 |
| 2016/0051169 A1* | 2/2016 | Hong | ............... | A61B 5/7455 600/595 |
| 2016/0058300 A1* | 3/2016 | Yoon | ............... | A61B 5/0059 600/480 |
| 2016/0066844 A1* | 3/2016 | Venkatraman | ...... | A61B 5/0002 702/141 |
| 2016/0084869 A1* | 3/2016 | Yuen | ............... | G01P 7/00 73/510 |
| 2016/0106327 A1* | 4/2016 | Yoon | ............... | A61B 5/02108 600/480 |
| 2016/0106333 A1* | 4/2016 | Kang | ............... | A61B 5/0059 600/301 |
| 2016/0150978 A1* | 6/2016 | Yuen | ............... | A61B 5/0205 600/301 |
| 2016/0157736 A1* | 6/2016 | Huang | ............... | A61B 5/0059 600/477 |
| 2016/0183818 A1* | 6/2016 | Richards | ............... | A61B 5/02427 600/479 |
| 2016/0198961 A1* | 7/2016 | Homyk | ............... | A61B 5/0082 600/476 |
| 2016/0278645 A1* | 9/2016 | Yoon | ............... | A61B 5/02141 |
| 2016/0278676 A1* | 9/2016 | Eisen | ............... | A61B 5/14551 |
| 2016/0278718 A1* | 9/2016 | Fujii | ............... | A61B 3/1233 |
| 2016/0302706 A1* | 10/2016 | Richards | ............... | A61B 5/02427 |

OTHER PUBLICATIONS

Draijer et al. "Review of laser speckle contrast techniques for visualizing tissue perfusion." Lasers MedSci 24:63-651 ; 2009.*

Jayanthy et al. "Non-Invasive Capillary Blood Flow Measurement: Laser Speckle and Laser Doppler." Intnl J Med, Health, Biomedical, Bioengineering and Pharmaceutical Engineering vol. 7, No. 5, 2011 : 205-210.*

Zalevsky et al. "A novel technique for remotely monitoring key biological parameters." SPIE Newsroom 10.1117/2.1201106.003742 (2011), 2 pages.*

Basak et al. "Review of laser speckle-based analysis in medical imaging." Med Biot Eng Comput (2012) 50:547-558.*

Lomer et al. "Speckle POF sensor for detecting vital signs of patients." Proc. of SPIE vol. 9157.91572I (2014), 4 pages.*

Beiderman et al. "Remote estimation of blood pulse pressure via temporal tracking of reflected secondary speckles pattern." J Biomedical Optics 15(6) (Nov./Dec. 2010), 7 pages.*

* cited by examiner

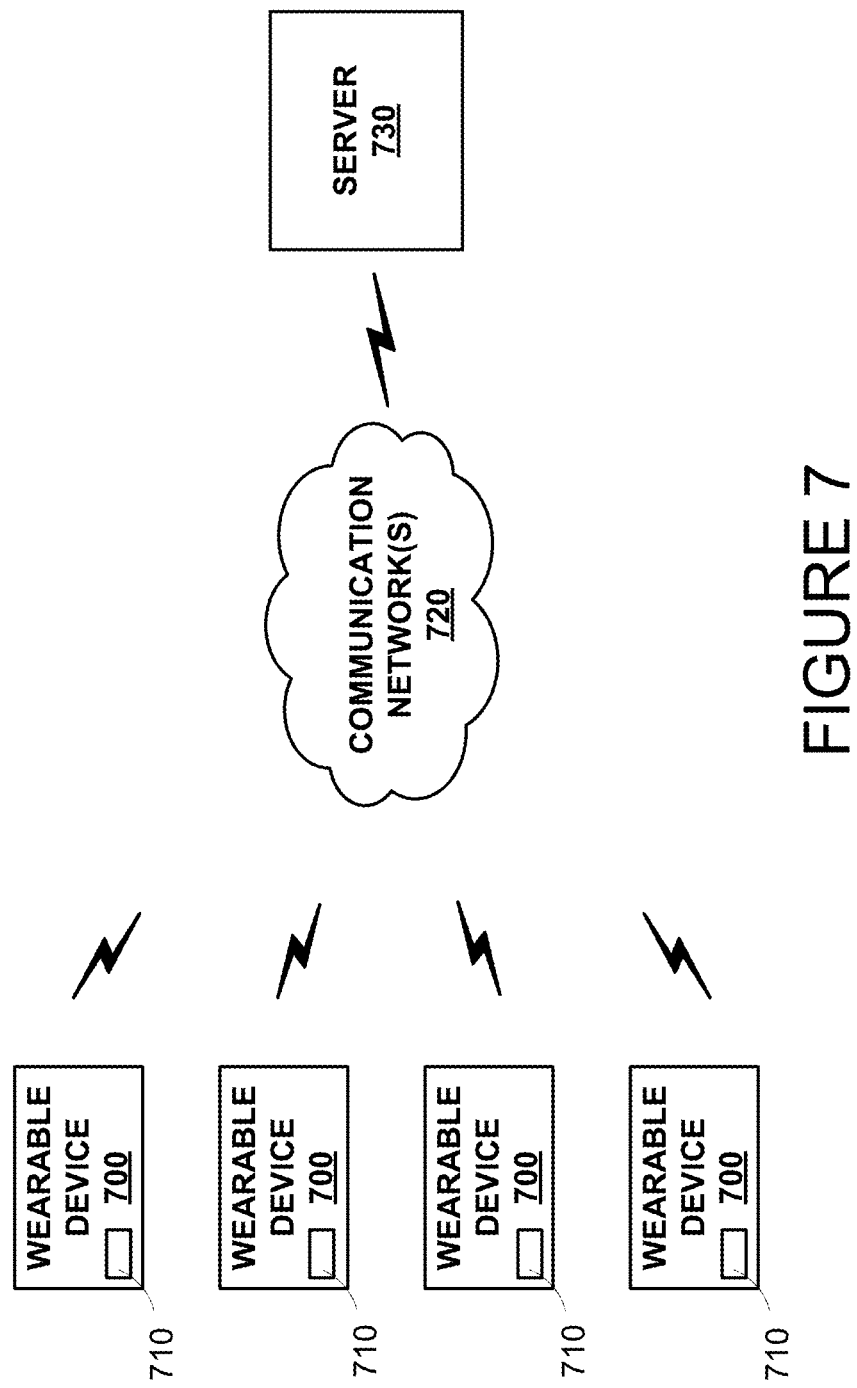

NON-INVASIVE FLOW MONITORING

BACKGROUND

Unless otherwise indicated herein, the materials described in this section are not prior art to the claims in this application and are not admitted to be prior art by inclusion in this section.

Illumination of a scattering environment (e.g., an environment containing rough surfaces or other scattering objects or features) by a source of coherent, monochromatic light (e.g., a laser) can result in light emitted (i.e., reflected, refracted, diffracted, or otherwise scattered) from the environment forming a speckle pattern. That is, constructive and destructive interference between coherent, monochromatic light that takes different paths through the scattering environment due to scattering by features of the environment, and that thus experiences different path lengths, can form a pattern of light and dark speckles across a surface (e.g., a planar array of light sensors). The speckle pattern can be related to the features of the scattering environment, such as the specific geometry of a rough surface and the locations, orientations, and properties of individual scattering objects (e.g., blood cells) in the environment).

SUMMARY

Some embodiments of the present disclosure provide a wearable device including: (i) a light source, wherein the light source is configured to emit a beam of coherent illumination into a portion of subsurface vasculature; (ii) a light sensor, wherein the light sensor is configured to detect a pattern of constructive and destructive interference in light emitted from the portion of subsurface vasculature in response to the coherent illumination from the light source; and (iii) a controller, wherein the controller is configured to (a) operate the light source and the light sensor and (b) determine a flow property in the portion of subsurface vasculature based at least on a time dependence of the pattern of constructive and destructive interference in light emitted from the portion of subsurface vasculature detected using the light sensor.

Some embodiments of the present disclosure provide a method including: (i) illuminating, by a light source, a portion of subsurface vasculature with a beam of coherent illumination, wherein the light source is disposed on a wearable device; (ii) detecting, using a light sensor, a pattern of constructive and destructive interference in light emitted from the portion of subsurface vasculature in response to the coherent illumination from the light source, wherein the light sensor is disposed on the wearable device; and (iii) determining a flow property in the portion of subsurface vasculature based at least on a time dependence of the pattern of constructive and destructive interference in light emitted from the portion of subsurface vasculature detected using the light sensor.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 7 is a block diagram of an example system that includes a plurality of wearable devices in communication with a server.

DETAILED DESCRIPTION

Figure 1:
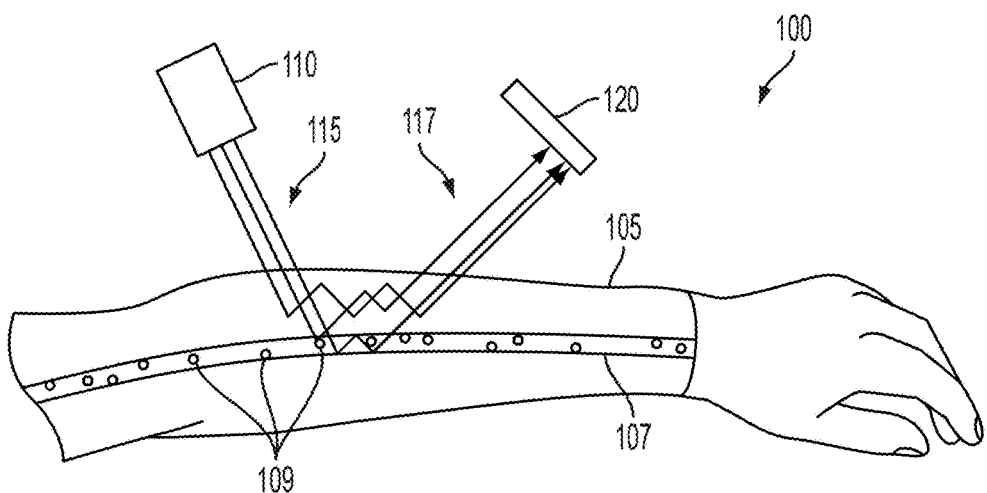
FIG. 1 is side partial cross-sectional view of an example system, while measuring blood flow in a human wrist.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where non-invasive detection of a flow property is desired. The environment may be any living or non-living body or a portion thereof, a gel, an emulsion, a fluid conduit, a fluid reservoir, etc. For example, one of skill in the art will recognize that the embodiments disclosed herein may be used to sense properties of fluid flow in a water treatment system. Moreover, while the present disclosure describes embodiments for use in vivo, one of skill in the art will also recognize that in vitro applications are possible as well. Accordingly, the environment may also include a test tube or other vessel for holding a fluid.

I. Overview

A property of flow in an environment (e.g., a mean velocity of a fluid flow in an environment, a peak velocity of scatterers in an environment, a distribution of velocities of scatterers in an environment) can be detected by illuminating the environment using a beam of light emitted by a laser (e.g., a substantially coherent, substantially monochromatic beam of light) and detecting a change over time of a pattern of constructive and destructive interference in light emitted by the environment in response to the illumination. That is, scattering of the illumination by scattering elements in the environment (e.g., cells in blood, smoke particles in air) could cause constructive and destructive interference between illuminating light that takes different paths through the scattering environment, thus forming a pattern of light and dark speckles when projected on a surface. A light sensor could be disposed on the surface and configured to detect the intensity (or some other property) of light emitted by the environment in response to the illumination. Changes in the detected level of intensity of the received light over time (i.e., a time-dependence of the pattern of constructive and destructive interference in the light emitted by the environment) could be used to determine the property of flow in the environment. For example, the duration, rise time, fall time, and/or some other property of speckle events (e.g., changes in the environment (e.g., translations or rotations of scattering particles) that cause a corresponding change in the speckle pattern) could be used to determine the property of flow in the environment.

The environment could be any environment that, when illuminated by a laser or other source of substantially coherent light, emits light having a pattern of constructive and destructive interference (e.g., a speckle pattern) related to the configuration of elements in the environment such that a change in the pattern of light can be related to a flow property of a region of the environment (e.g., a velocity of flow of a liquid in the environment). The environment could include gases, liquids, gels, or other fluids. The environment can include a population of scattering agents, i.e., small particles or other objects or features configured to move with a fluid flow and to reflect, refract, diffract, or otherwise scatter light. Examples of such scattering agents and environments include blood cells and other particles in blood, particles of water or ice in a fog, and solid and liquid particulates in smoke. In some examples, the laser, light sensor, and/or other elements of systems for measuring flows as described herein could be disposed proximate to the environment of interest; in other examples, the components of the flow-measuring systems could be disposed at a distance from an environment of interest. In some examples, a scattering agent (e.g., dielectric nanoparticles, fog, smoke, cavitation bubbles) could be introduced into and/or induced in an environment of interest to enable detection of a flow property of a region of the environment of interest. In some examples, the scattering agent could include cavitation bubbles induced in a region of the environment of interest, e.g., by emitting ultrasonic energy in to the environment of interest.

Changes in the arrangement of scattering agents or other scattering features within the environment can cause a change in the pattern of light (i.e., the speckle pattern) emitted by the environment in response to illumination by a laser or other light source that emits a beam of coherent illumination. For example, displacement of scattering features disposed in a fluid due to flow of the fluid can cause a change in the pattern of light that is related to the direction, velocity, or other properties of the fluid, the fluid flow, and/or the location and orientation of the scattering features. When the intensity of the speckle pattern is measured in a specified region (e.g., at a 'point' corresponding to the location of a light sensor), time dependent features of the measured intensity (i.e., a waveform of the measured intensity) can be related to a flow property and/or other properties of the environment. For example, movements of the scattering features can cause the specified region to experience a 'speckle event', wherein the intensity of the light received from the environment increases/decreases suddenly, followed by a sudden decrease/increase. Such a pulse in the intensity could take the form of a quasi-trapezoidal pulse, a raised-cosine pulse, or some other pulse shape. Further, one or more properties of the speckle event pulse (e.g., a rise time, a fall time, a pulse width, a pulse amplitude) could be related to a flow property (e.g., a velocity of an individual scattering feature in a fluid flow or a distribution of velocities of individual scattering features in a fluid flow) of the environment. Other properties (e.g., a rate of change) of the measured intensity level over time could be related to a flow property of the environment.

In some examples, the intensity of the received light (as detected using a light sensor) could be sampled at a high rate by an analog-to-digital converter, and subsequent processing could be performed by a processor or other computational substrate, based on the sampled intensity information, to determine a flow property of the environment. In some examples, analog circuitry (e.g., operational amplifiers, filters, comparators, sample-and-holds, peak detectors, differentiators) could be included to perform some analog computation on the output of the light sensor. For example, a rate of change (i.e., slope) of the output of the light sensor could be computed using a differentiator, and the output of the differentiator could be passed to a peak detector, such that the output of the peak detector could be related to the velocity of the highest-velocity scattering feature to have caused a speckle event as measured by a light sensor during a specified period of time. Additional or alternative methods of using the output of a light sensor to determine a flow property of an environment are anticipated.

In some embodiments, multiple light sources (e.g., lasers) could be configured to emit beams of illumination having different wavelengths and/or from different angles or locations relative to an environment of interest and/or relative to a light sensor(s) to determine one or more flow properties of the environment or sub-regions thereof or according to some other application. In some embodiments, a plurality of light sensors could be disposed at a plurality of locations relative to an environment of interest and/or relative to an illuminating laser(s) to determine one or more flow properties of the environment of interest (or a subsection thereof) or according to some other application. In some examples, the plurality of sensors could be part of a single integrated circuit. In some examples, each individual light sensor of the plurality of light sensors could have a respective set of analog or other electronic components as described herein to enable detection of a flow property of a region of an environment.

The above described system may be implemented as a wearable device. The term "wearable device," as used in this disclosure, refers to any device that is capable of being worn at, on, or in proximity to a body surface, such as a wrist, ankle, waist, chest, ear, eye or other body part. In order to take in vivo measurements in a non-invasive manner from outside of the body, the wearable device may be positioned on a portion of the body where subsurface vasculature or some other flow environment is easily observable. The device may be placed in close proximity to the skin or tissue, but need not be touching or in intimate contact therewith. A mount, such as a belt, wristband, ankle band, headband, etc. can be provided to mount the device at, on or in proximity to the body surface. The mount may prevent the wearable device from moving relative to the body to reduce measurement error and noise. Further, the mount may be an adhesive substrate for adhering the wearable device to the body of a wearer. The light sensor, laser, and, in some examples, a processor and/or other components, may be provided on the wearable device.

In other embodiments, the above described system may be implemented as a stationary measurement device that a user may be brought into contact or proximity with or as a device that may be temporarily placed or held against a body surface during one or more measurement periods. In other embodiments, the above described system may be implemented to interrogate an environment that is not a part of a human body, e.g., an in vitro or other sample container, an outdoor environment, an animal body, or some other environment of interest that can scatter a laser-emitted beam of illumination in a manner related to a flow property of the environment (or a subsection thereof).

It should be understood that the above embodiments, and other embodiments described herein, are provided for explanatory purposes, and are not intended to be limiting.

II. Illustrations of Flow Property Detection

Flow properties (e.g., a flow rate) of fluid in an environment (e.g., blood in a portion of vasculature, a liquid, gel, emulsion, gas, or other flowing material in an industrial or other environment) can be detected by a variety of methods related to properties of the fluid and of the environment. In examples wherein the environment contains scatterers (i.e., particles that can scatter incident illumination and that can be affected by a fluid or other flow in the environment), a flow property of the environment could be detected and/or determined by illuminating the environment and detecting a time-dependence of a pattern, intensity, or other property of illumination scattered by the scatterers.

FIG. 1 is a partial cross-sectional side view of a human arm 105 illustrating the operation of an example system 100. In the example shown in FIG. 1A, the system 100 includes a laser 110 configured to emit a beam of coherent illumination 115 into tissue of the arm 105 including a portion of subsurface vasculature 107 containing blood cells 109 (i.e., scatterers). The system 100 additionally includes a light sensor 120 configured to detect a pattern of constructive and destructive interference in a portion of the beam of coherent illumination 115 that is scattered by tissue of the arm 105 and that is emitted as an emitted light 117 toward the light sensor 120. The system 100 additionally includes a controller (not shown) configured to operate the laser 110 and the light sensor 120 to determine a flow property (e.g., a flow rate) of blood in the portion of subsurface vasculature 107. The system 100 could include further elements, e.g., a housing within which the laser 110, light sensor 120, and/or controller could be disposed, a mount configured to mount the laser 110 and light sensor 120 to the arm 105, or some other elements.

The pattern of constructive and destructive interference in the emitted light 117 can be the result of individual portions of the beam of coherent illumination 115 being scattered by different scattering (e.g., reflecting, refracting, diffracting) elements in the arm 105 (e.g., cell walls, blood cells, cell elements, tissue boundaries, chromophores, fat globules, or other reflective elements/boundaries and/or discontinuities in refractive index) and thus experiencing different paths lengths between emission at the laser 110 and reception at the light sensor 120. The different portions of the beam of coherent illumination 115 (having been scattered toward the light sensor in the form of the emitted light 117), are thus out of phase and will constructively and/or destructively interfere with each other in a manner related to respective amplitudes and relative phases of the portions of the emitted light 117 to form a pattern of constructive and destructive interference at the light sensor 120 and/or at other locations in the vicinity of the system 100 and arm 105.

Thus, the pattern of constructive and destructive interference in the emitted light 117 can be related to a configuration of elements of the arm 105 (e.g., to the location of blood cells 109 in the portion of subsurface vasculature 107). The light sensor 120 detecting the pattern of constructive and destructive interference can include the light detector 120 being configured and/or operated to detect any property or properties of the pattern of constructive interference having a time dependence that can be used to determine a flow property of blood in the portion of subsurface vasculature 107. In some examples, this could include the light sensor 120 being configured to detect the intensity and/or some other property of the emitted light 117 at a single point (e.g., using a single photodetector or other light-sensitive element disposed at a specified location relative to the laser 110 and/or elements of the arm 105). In some examples, this could include the light sensor 120 being configured to detect the intensity and/or some other property of the emitted light 117 at multiple points (e.g., using two or more photodetectors or other light-sensitive elements). In some examples, the light sensor 120 could be a camera (i.e., an aperture, an array of photodetectors, and/or optics) and detecting the pattern of constructive interference could include detecting the amplitude of the emitted light 117 that is received by the camera from various locations (e.g., from various respective angles relative to the camera) of the arm 105. Other configurations and operations of one or more light sensors (e.g., 120) to detect the pattern of constructive and destructive interference in the emitted light 117 are anticipated.

Further, detecting the pattern of constructive and destructive interference in the emitted light 117 could include detecting additional or alternative properties of the pattern of constructive and destructive interference. Detected properties of the pattern of constructive and destructive interference could include the intensity, wavelength, spectrum, degree of polarization, direction of polarization, or some other property of light at a specified location(s) in the pattern and/or from a particular direction (e.g., from a particular location of the arm 105 and/or from a particular direction relative to a photodetector or other light sensitive element). Detected properties of the pattern of constructive and destructive interference could include properties of an image formed by the pattern of constructive and destructive interference (e.g., an image detected using a camera, an array of photodetectors on a surface, or some other image-detecting apparatus); for example, a contrast ratio, a speckle location, a speckle size, a number of speckles, a speckle shape, an overall pattern width, or some other property or properties.

Figure 2:
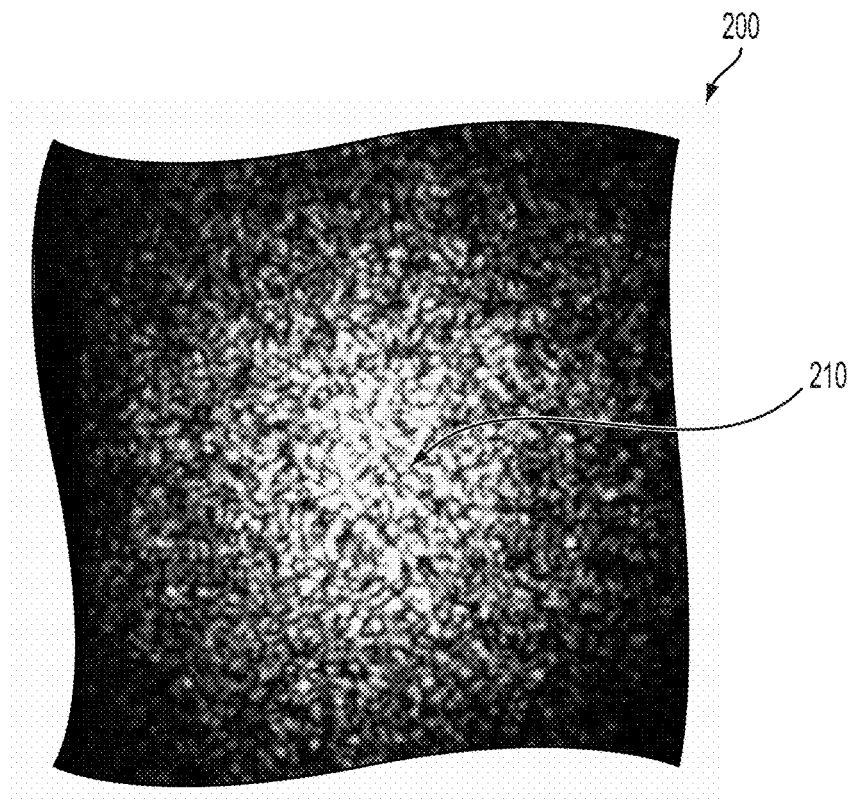
FIG. 2 is an example image of a speckle pattern emitted by a scattering medium that is illuminated by laser light.

FIG. 2 illustrates an example speckle image 200 that could be generated on an imaging surface (e.g., a surface of the light sensor 120) in response to illumination of a scattering environment (e.g., the arm 105, portion of subsurface vasculature 107, and blood cells 109) by light emitted from the environment (e.g., 117) in response to a beam of coherent illumination (e.g., a beam 115 emitted by the laser 110). The speckle image 200 includes a plurality of speckles 210 corresponding to where the constructive and destructive sum of the light impinging on a corresponding region of the imaging surface results in an overall higher level of light intensity than in other regions of the speckle image 200. Properties of the pattern of constructive and destructive interference that results in the speckle image 200 are related to properties of the scattering environment (e.g., location of scattering elements in the environment, refractive index of elements of the environment), properties of the illuminating beam of coherent illumination (e.g., a wavelength, a spectral line width, an intensity, a coherence length, a beam width, a beam polarization), and of the imaging surface on which the speckle image 200 is formed (e.g., the location of the imaging surface relative to the beam of coherent illumination and the environment). Thus, time-dependent changes in the configuration of the environment (e.g., movement of scatterers in a fluid flow in the environment) could result in a time-dependent change in the pattern of constructive and destructive interference in the light emitted by the environment that could further results in a time-dependent change in the imaged speckle pattern 200. That is, the location, number, size, shape, intensity, or other properties of speckles 210 or other features of the speckle pattern 200 could change in a time-dependent manner related to a change in the environment and/or a change in the location of the imaging surface and/or source of the beam of coherent illumination relation to the environment.

The pattern of constructive and destructive interference represented by the speckle image 200 could be related to reflection, refraction, diffraction, scattering, absorption, or other interactions between a beam of coherent light illuminating an environment and elements of the environment. For example, interfaces between regions of the environment having different indices of refraction (e.g., at a cell wall, at the wall of a portion of vasculature, at the surface of a bone, at the surface of a muscle, at a skin surface, at some other interface in a biological or other environment) can cause scattering, refraction, reflection, and/or other interactions with light. Other elements of an environment (e.g., metallic and/or semiconductive particles, surfaces, or other elements) could cause reflection, scattering, and/or other interactions with illuminating light in a manner related to the pattern of constructive and destructive interference represented by the speckle image 200.

FIGS. 3A-3E illustrate the operation of an example system 300 that could be operated to determine a flow property (e.g., a flow rate) of blood in a portion of subsurface vasculature 307 in an arm 305. The system 300 includes a laser 310 configured to emit a beam of coherent illumination 315 into tissue of the arm 305 that includes the portion of subsurface vasculature 307 and blood cells (e.g., illustrative blood cell 309) contained in the portion of subsurface vasculature 307 that move along with blood in the portion of subsurface vasculature 307. The system 300 additionally includes a light sensor 320 configured to detect a pattern of constructive and destructive interference in a portion of the beam of coherent illumination 315 that is scattered by tissue of the arm 305 and that is emitted as an emitted light 317a, 317b, 317c toward the light sensor 320. The system 300 additionally includes a controller (not shown) configured to operate the laser 310 and the light sensor 320 to determine a flow property (e.g., a flow rate) of blood in the portion of subsurface vasculature 307. The system 300 could include further elements, e.g., a housing within which the laser 310, light sensor 320, and/or controller could be disposed, a mount configured to mount the laser 310 and light sensor 320 to the arm 305, or some other elements.

Figure 3A:
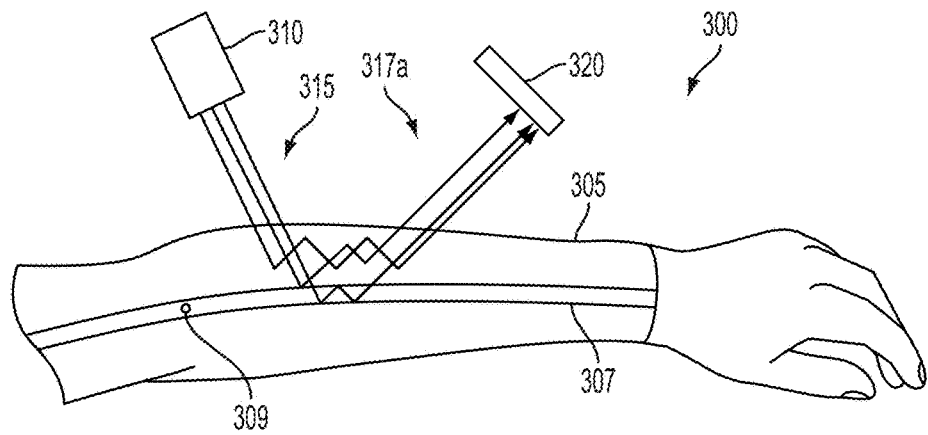
FIG. 3A is side partial cross-sectional view of an example system, while measuring blood flow in a human wrist.
Figure 3B:
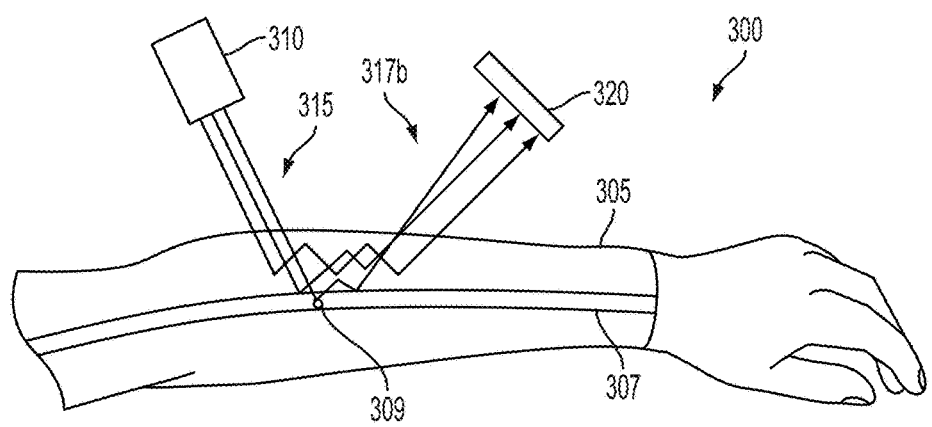
FIG. 3B is side partial cross-sectional view of the example system illustrated in FIG. 3A, while measuring blood flow in a human wrist.
Figure 3C:
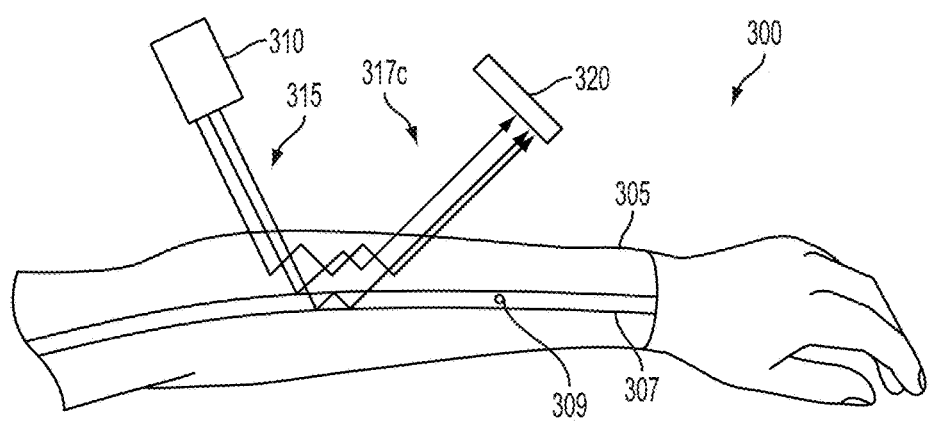
FIG. 3C is side partial cross-sectional view of the example system illustrated in FIG. 3A, while measuring blood flow in a human wrist.
Figure 3D:
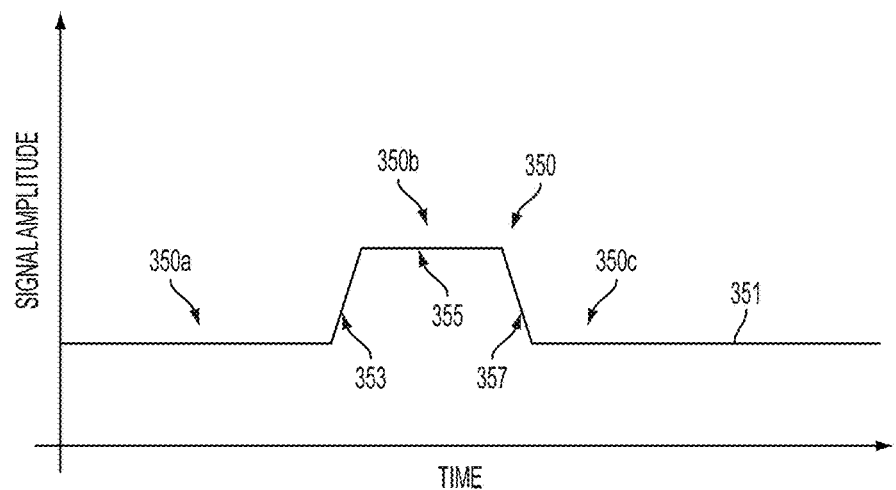
FIG. 3D is an example output generated by the example system illustrated in FIGS. 3A-3C.

To illustrate the operation of the system 300, the movement of an illustrative blood cell 309 due to blood flow in the portion of subsurface vasculature 307 is illustrated in FIGS. 3A-3C and the corresponding time-dependent changes of the pattern of constructive and destructive interference detected by the light sensor 320. Specifically, FIG. 3D illustrates an example detected light intensity waveform 351 corresponding to the intensity of the pattern of constructive and destructive interference at a specified point as detected by the light sensor 320.

FIG. 3A illustrates the system 330 and arm 307 at a first period of time. The illustrative blood cell 309 is in an upstream region of the portion of subsurface vasculature 307 that is substantially outside of a region illuminated by the beam of coherent illumination 315. As a result, the light sensor 320 detects a first light intensity 350a related to a pattern of constructive and destructive interference in first emitted light 317a.

FIG. 3B illustrates the system 330 and arm 307 at a second period of time. The illustrative blood cell 309 is moved downstream due to blood flow into the region of the portion of subsurface vasculature 307 that is illuminated by the beam of coherent illumination 315 and thus acts to scatter the beam of coherent illumination 315. As a result, the light sensor 320 detects a second light intensity 350b related to a pattern of constructive and destructive interference in second emitted light 317b that is substantially different from the pattern of constructive and destructive interference in first emitted light 317a.

FIG. 3C illustrates the system 330 and arm 307 at a third period of time. The illustrative blood cell 309 is moved downstream due to blood flow into a downstream region of the portion of subsurface vasculature 307 that is substantially outside of the region illuminated by the beam of coherent illumination 315. As a result, the light sensor 320 detects a third light intensity 350c related to a pattern of constructive and destructive interference in third emitted light 317c that is substantially similar to the pattern of constructive and destructive interference in first emitted light 317a.

The movement of the illustrative blood cell 309 through the portion of subsurface vasculature 305 in the first, second, and third periods of time (as illustrated in FIGS. 3A-C, respectively) results in the light sensor 320 detecting an illustrative speckle event 350 in the detected light intensity waveform 351. The illustrative speckle event 350 is a trapezoidal pulse that includes a rising edge 353, a plateau 355, and a falling edge 357. One or more of these elements could be related to the speed of the illustrative blood cell 309 and thus to a flow property of the blood in the portion of subsurface vasculature. In some examples, a time property (e.g., a rise time of the rising edge 353, a duration of the plateau 355, a fall time of the falling edge 357) of the speckle event 350 could be related to a speed of the illustrative blood cell 309. For example, the rate of increase in intensity during the rising edge 353 could correspond to the velocity of the illustrative blood cell 309 such that higher rates correspond to higher velocities.

Note that the movement of the illustrative blood cell 309 and the corresponding detected light intensity waveform 351 are meant as illustrative examples. A portion of subsurface vasculature could include many blood cells having respective different velocities related to the movement of blood in the portion of subsurface vasculature. Further, the movement of an individual blood cell through a region of subsurface vasculature illuminated by a coherent light source could result in no speckle event, multiple speckle events, or some other feature(s) to be present in a detected light intensity waveform or other detected signal related to the pattern of constructive and destructive interference in a portion of a beam of coherent illumination that is scattered the environment including the portion of subsurface vasculature and blood cell(s)) and that is emitted as an emitted light toward a light sensor.

Figure 3E:
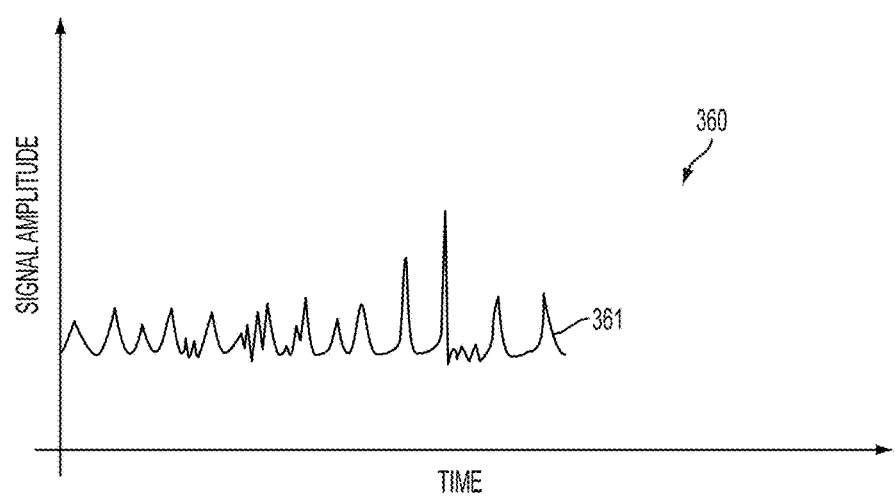
FIG. 3E is an example output generated by the example system illustrated in FIGS. 3A-3C.

FIG. 3E shows an example detected light intensity waveform 361 that could be detected using the system 300 when a plurality of blood cells and other scatterers are being moved in a flow of blood in the portion of subsurface vasculature 307. The detected light intensity waveform 361 includes a plurality of speckle events having respective shapes, durations, amplitudes, rise/fall times, and/or other properties. The system 300 could include electronics (e.g., amplifiers, filters, comparators, envelope detectors, slope detectors, differentiators, peak detectors, ADCs, microprocessors, microcontrollers) configured to determine one or more flow properties of the blood in the portion of subsurface vasculature based on the detected light intensity waveform 361. For example, the electronics could be configured to detect a rise time of individual speckle events in the detected light intensity waveform 361 and to determine a corresponding blood cell velocity. The electronics could be further configured to determine a distribution of velocities of individual blood cells in the blood, a mean flow rate of the blood, and/or some other flow property of the blood in the portion of subsurface vasculature.

Determined flow properties of an environment (e.g., of blood in a portion of subsurface vasculature) could be any properties or physical parameters relating to a flow of a fluid within the environment. In some examples, determined flow properties could include the velocity, direction, acceleration, or other information about the movement of individual particles (e.g., blood cells or other scatterers) or groups of particles within the environment. For example, a system could determine the velocity of individual particles in the environment based on a detected temporal property of speckle events or other features of a detected waveform that is related to a pattern of constructive and destructive interference in light emitted by the environment in response to illumination by a beam of coherent light. In some examples, determined flow properties could include properties describing a bulk flow of fluid, e.g., a flow rate, a mean flow velocity, a mean flow speed, a mass flow rate, or some other property of a fluid flow in an environment. In some examples, the detected flow property could correspond to a subsection or other specified region of an environment, e.g., blood in a portion of subsurface vasculature in an arm or other portion of anatomy. The location of the specified region could be related to the configuration of the system (e.g., the location and direction of a laser, the location and direction of sensitivity of a light sensor). For example, a laser of the system could be configured to emit a beam of coherent illumination in a specified direction relative to the laser, and a light sensor could be configured to detect a property of light received from a specified direction relative to the light sensor, such that the determined flow property is a flow property of fluid proximate to the intersection of the beam of coherent illumination and a vector extending from the light sensor in the specified direction relative to the light sensor.

The laser 310 could be configured in a variety of ways and include a variety of elements such that the emitted beam of coherent illumination 315 has one or more specified properties according to an application. The beam of coherent illumination 315 could have a specified wavelength. In some examples, the wavelength of the beam of coherent illumination 315 could be specified such that it could penetrate an environment of interest, be scattered by scatterers in a fluid flow in the environment of interest, or according to some other considerations. For example, the environment could be a portion of subsurface vasculature within a portion of human anatomy, the determined flow property could be a flow property of blood within the portion of subsurface vasculature, and the wavelength of the beam of coherent illumination 315 could be between approximately 400 nanometers and approximately 1000 nanometers. In some examples, the wavelength of the beam of coherent illumination 315 could be specified relative to a characteristic size or other property of scatterers (e.g., blood cells, cavitation bubbles, natural and/or artificial particles, bubbles or gas or other material having dissimilar optical properties to a surrounding fluid medium) such that the scatterers could scatter the beam of coherent illumination 315 and cause the environment to emit light having a pattern of constructive and destructive interference related to the configuration of the environment and/or scatterers. The wavelength of the beam of coherent illumination 315 could be within a near-infrared (NIR) transparency window of biological tissue (e.g., between approximately 780 and approximately 810 nanometers).

In some examples, the beam of coherent illumination 315 could have a coherence length that is greater than some minimum coherence length (e.g., greater than 1 millimeter) that is related to scattering properties of elements of the environment (e.g., skin cells, connective tissue, portions of subsurface vasculature, blood cells, and other elements of a human arm or other portion of human anatomy). The specified minimum coherence length could be related to a spacing of scatterers or other optical features (e.g., reflecting, refracting, and/or diffracting interfaces between regions having different indices of refraction, metallic and/or semiconductive elements) in the environment such that one or more properties of a pattern of constructive and destructive interference can be detected and used to determine a flow property of the environment. Further, the laser 310 could include a volume holographic grating, a monochromator, a Lyot filter, a Bragg reflector, a dielectric mirror, or some other element(s) configured to increase a coherence length of and/or decrease a spectral line width of the beam of coherent illumination 315. Such elements could be disposed on a discrete laser (e.g., a volume holographic grating could be disposed in the path of the beam of a laser) and/or could be incorporated into one or more elements of the laser 310 (e.g., mirrors, lenses, gain media, frequency doublers, or other elements of the laser 310 could be configured such that they had properties of one or more of the listed additional elements).

The laser 310 could be selected from a wide variety of lasers according to an application. The laser 310 could include a gas laser, a chemical laser, a dye laser, a metal-vapor laser, a solid-state laser, a semiconductor laser, or any other type of laser configured to produce a beam of coherent illumination having one or more specified properties (e.g., wavelength, spectral line width, coherence length) such that the laser could illuminate an environment of interest (e.g., a portion of subsurface vasculature 307) that contains light-scattering elements (e.g., blood cells, human tissue) such that the environment of interest responsively emits light having a pattern of constructive and destructive interference that has one or more time-dependent properties that can be detected and used to determine a flow property (e.g., a flow rate of blood) of the environment. In some applications, the system 300 could be a wearable device and the laser 310 could be configured to satisfy limited power and space requirements of the wearable device such that the system 300 could be battery-powered and could be comfortably worn by a wearer (e.g., worn around a wrist of the wearer).

For example, the laser 310 could be a small laser diode, e.g., a VCSEL, a double heterostructure laser, a quantum well laser, or some other structure of semiconductor laser incorporating gallium nitride, indium gallium nitride, aluminum gallium indium phosphide, aluminum gallium arsenide, indium gallium arsenide phosphide, lead salt, or some other material or combination of materials as a gain medium. In some examples, the laser 310 could include frequency doublers, optics, collimators, or some other elements according to an application. In some examples, the laser 310 could be incorporated into other elements of the system 300. For example, the laser 310 could be wire-bonded, soldered, or otherwise electronically and/or mechanically coupled to a circuit board or other element(s) of the system, 300. Additionally or alternatively, the laser 310 or elements thereof could be incorporated into a single semiconductor device (e.g., wafer or chip) with other components (e.g., a laser power supply, a microcontroller). Further, the laser 310 could be configured to control the direction of the beam of coherent illumination 315 (e.g., by including servos, motors, piezo elements, or other actuators configured to translate and/or rotate the laser and/or optics or other elements thereof) to enable detection of flow properties in specified sub-regions of the arm 305 (e.g., different regions of the portion of subsurface vasculature 307, different portions of subsurface vasculature (not shown)) by directing the beam of coherent illumination 315 toward the different specified sub-regions of the arm 305.

In some examples, the system 300 could include more than one laser. Individual lasers of the more than one laser could have respective specified properties (e.g., locations, angles and/or locations of emitted beams of coherent illumination, wavelengths, coherence lengths, polarizations) according to an application. More than one laser could be provided to allow for detection of a flow property in more than one region of the arm 305 (e.g., multiple locations of the portion of subsurface vasculature 307, other portions of tissue in the arm 305). In some embodiments, the system 300 could include a spatially distributed array of lasers configured such that individual lasers of the array emit beams of coherent illumination into respective individual subregions (e.g., overlapping or non-overlapping portions of tissue) of the arm 305. Such an array of lasers could be operated to determine a corresponding plurality of flow properties of the respective individual subregions of the arm 305 (e.g., to determine a flow map within the arm 305, to determine a location, shape or other property of vasculature in the arm 305, or according to some other application). More than one laser could be provided to enable higher-accuracy or otherwise improved detection of a flow property of blood or other fluid (e.g., by providing a redundant source of coherent illumination, by allowing illumination of a single region of the portion of vasculature from multiple angles, by providing multiple wavelengths of illumination for detection).

More than one laser could be provided to enable measurement of more than one flow property. For example, a first laser could emit a beam having a first wavelength that is preferentially scattered by a first population of scatterers in the environment (e.g., portion of subsurface vasculature) and a second laser could emit a beam having a second wavelength that is preferentially scattered by a second population of scatterers in the environment such that the first and second lasers could be operated, in combination with one or more light sensors, to determine a first flow property of the environment related to movement of the first scatterers and a second flow property of the environment related to movement of the second scatterers.

The light sensor 320 could include any variety of light-detecting apparatus configured to detect a pattern of constructive and destructive interference in light that is emitted by an environment (e.g., 305, 307) and that is related to the configuration of the environment and/or scatterers therein. The light sensor 320 could include one or more photodetectors, photodiodes, phototransistors, CCDs, active pixel sensors, photoresistors, or other light-sensitive elements. The light sensor 320 could be configured to detect an intensity, a wavelength, a spectrum, a degree of polarization, a direction of polarization, or some other property of light emitted by the environment and received at one or more locations on or within the light sensor 320. For example, the light sensor 320 could be configured to detect the intensity of light received in a specified region (i.e., a sensitive region of the light sensor 320) relative to the arm 305 that is received from a direction toward the portion of subsurface vasculature 305 relative to the light sensor 320. In some examples, the light sensor 320 could include a camera (e.g., an aperture, a plurality of individual light-sensitive elements (e.g., a CCD, an array of active pixel sensors), and/or optics).

In some examples, the system 300 could include more than one light sensor (e.g., a plurality of light sensors) disposed at more than one location relative to the laser 310, arm 305, or other elements of an environment of interest. The more than one light sensor could be provided to allow for detection of a flow property in more than one region of the arm 305 (e.g., multiple locations of the portion of subsurface vasculature 307, other portions of tissue in the arm 305). The more than one light sensor could be provided to enable higher-accuracy or otherwise improved detection of a flow property of blood or other fluid (e.g., by providing a redundant source of information about a pattern of constructive and destructive interference in light emitted by an environment, by allowing detection of multiple patterns of constructive and destructive interference emitted by the portion of vasculature toward multiple angles, by providing detection of multiple wavelengths of emitted light).

The light sensor 320 could include a variety of components according to an application. The light sensor 320 could include lenses, polarization filters, color filters, apertures, mirrors, diffraction gratings, liquid crystal elements, baffles, or other optical elements to affect the light received by the light sensor 320. In some examples, the light sensor 320 could include a color filter configured to substantially block light having wavelengths different from a wavelength of light emitted by the laser 310. In some examples, the light sensor 320 could include an aperture, lenses, or other element(s) configured to make the light sensor 320 electively sensitive to light coming from a particular direction(s)

relative to the light sensor 320, laser 310, or other elements of the system 300 and/or the arm 305. For example, the light sensor 320 could be configured to be selectively sensitive to light emitted from a specified region of the portion of subsurface vasculature 307. In some examples, the size of the specified region could be specified such that a bandwidth or other time-dependent property of a signal produced and/or detected by the light sensor 320 (e.g., a rate of speckle events detected by the lights sensor 320) is within some specified limit(s). For example, the specified region could be a region having a diameter or other characteristic size between approximately 100 microns and approximately 1 millimeter.

In some examples, the light sensor 320 could include an annular filter (i.e., a ring-shaped aperture disposed in front of a light-sensitive element of the light sensor 320). The annular filter could be configured to substantially block light from being received by the light sensor 320 unless the light approaches the light sensor 320 from an angle relative to a specified axis of the light sensor 320 (e.g., an optical axis of the sensor) that is within a specified range of angles. The specified range of angles could be specified related to a scattering property of the environment of interest (e.g., tissue of an arm 305 that includes blood flowing in a portion of subsurface vasculature 307). For example, the range of angles could be specified such that light received by the light sensor 320 is light that has been scattered a specified number of times and/or that has a statistical distribution of number of scattering events/collisions that has one or more specified properties (e.g., mean number of scattering events/collisions, variance of number of scattering events/collisions).

Note that the example speckle event 350 and other features of the example detected light intensity waveform 361 illustrated in FIGS. 3D and 3E, respectively, are meant as illustrative examples of signals related to patterns of constructive and destructive interference in light emitted from an environment of interest that could be used to determine a flow property of the environment. Rise times, rise rates, pulse widths, fall times, fall rates, and other temporal features of such detected signals are non-limiting examples of time-dependent waveform features that could be used to determine a flow property of an environment. Additionally or alternatively, an envelope, a spectrum, a derivative, a power in one or more frequency bands, a speckle or other event rate, an autocorrelation, or some other time-dependent variable or variables related to such detected signals could be used to determine a flow property of an environment. In examples wherein multiple physical features of patterns of constructive and destructive interference in emitted light are detected, additional or alternate time-dependent methods and/or derived variables could be used to determine a flow property of an environment based on the multiple detected physical features. For example, where the light sensor 320 includes a camera or some other array of light sensing elements (e.g., a rectangular array of photodetectors arranged on a surface), one or more properties of an image generated by the light sensor 320 could be used to determine a flow property of the environment. For example, a contrast level, a spatial correlation, a number of speckles in the image, a shape of speckle in the image, a change over time (e.g., a displacement, a change in size and/or shape) of the speckles in the image, or some other property of an image generated by the light sensor 320 could be determined and used to determine a flow property of the environment.

Determining a flow property of the environment could include sampling an output of the light sensor 320 (e.g., a detected light intensity at a specified location) at a sufficiently high frequency to determine and/or detect information in the output (i.e., to detect the output at a plurality of respective points in time) that is related to the flow property. For example, a controller or other elements of the system 300 could operate a high-speed analog-to-digital converter (ADC) of the system 300 to sample an output (e.g., a voltage, a current) of the light sensor 320 at a specified high rate (e.g., one megahertz) to detect features of individual speckle events in the output that have one or more properties (e.g., a pulse width, a rise time, a rise rate) related to a flow property of blood in the portion of subsurface vasculature 307. The specified high rate of sampling could be related to the duration, frequency, or some other temporal property of the output (e.g., an expected minimum duration of speckle events). For example, a speckle event could be expected to last approximately 1 microsecond, so the specified sample rate could be sufficiently in excess of 1 megahertz to resolve features of interest (e.g., a rising edge, a plateau, a falling edge) of individual speckle events.

Additionally or alternatively, the system 300 could include an analog frontend that includes analog circuitry configured to filter, decimate, quantize, or otherwise alter and/or perform other analog operations or computations on the output of the light sensor 320 to produce an output electronic signal that is related to the flow property of the environment (e.g., a flow property in the portion of subsurface vasculature). This output electronic signal could then be used (e.g., sampled by an ADC of a microcontroller) to determine the flow property. In examples wherein the light sensor 320 has a plurality of electronic outputs (e.g., a plurality of voltage outputs relating to the amplitude of light detected by a plurality of light-sensitive elements) and/or wherein the system 300 includes a plurality of light sensors, the system 300 could include a plurality of such analog frontends configured to receive respective outputs from respective lights sensors/elements of light sensors and to output respective electronic signals related to the respective received sensor output signals. Additionally or alternatively, the system 300 could include fewer instances of such an analog frontend, and the outputs of respective light sensors could be electronically multiplexed such that the fewer instances of the analog frontend could be operated in combination with the outputs of the respective light sensors.

An analog frontend as described above could include a variety of components configured in a variety of ways to generate output electronic signals having a variety of properties related to the flow property of the environment. In one example, a rate of change of the output signal of the light sensor 320 (e.g., a rise rate of rising edges of speckle events) could be related to the velocity of a corresponding scatterer in the environment. The analog frontend could include a differentiator configured to output a signal related to a rate of change of the output signal of the light sensor 320. The differentiator could be passive (e.g., an RC and/or RL filter circuit), active (e.g., an op-amp configured with capacitors, resistors, and/or other elements as a differentiator), or some combination thereof. Further, the differentiator could be configured to output a signal that is related to the rate of change of the output signal of the light sensor 320; for example, the differentiator could output a low-passed, rectified, or otherwise altered version of the rate of change of the output signal of the light sensor 320. The analog frontend could additionally include a peak detector configured to output a signal related to the maximum value of the signal output by the differentiator during a specified previous time period. The peak detector could include passive and active components configured in a variety of ways. In some examples, the peak detector could include an op-amp, a rectifier, and a capacitor configured to output a signal equal to the maximum value of the input to the peak detector in the past. This variety of peak detector could additionally include a reset electronic switch that could be operated to reset the peak detector, allowing the peak detector to output a signal equal to the maximum value of the input to the peak detector during a previous time period specified by the operation of the electronic switch. Additionally or alternatively, the peak detector could include a lossy integrator. The output of the peak detector could form the output of the analog frontend, and could be used to determine a flow property of the environment (e.g., by sampling the output using an ADC at one or more points in time and operating a microcontroller based on the digital output(s) of the ADC).

Additional or alternative analog and/or digital components and/or combinations of such with circuitry described herein could be configured and/or operated to enable determination of a flow property of an environment based on signals output from the light sensor 320. For example, the system 300 could include a plurality of light sensors, and the outputs of a first subset of the light sensors could be sampled at a high rate by high-frequency ADCs and the outputs of a second subset of the light sensors could be input into respective analog frontends as described herein. In another example, analog circuitry could be configured to detect the presence of a speckle event in the output of a light sensor, and a high-frequency ADC could be operated responsively to sample the output of the light sensor for a specified period of time after the detection of the speckle event by the analog circuitry (i.e., the operation of the ADC could be triggered by the detection of the speckle event by the analog circuitry). Other embodiments of analog and/or digital circuitry to determine one or more flow properties of an environment based on the outputs of one or more light sensors are anticipated.

Note that the detection of flow properties of blood in a portion of subsurface vasculature 307 of an arm 305 based on scattering of coherent illumination by scatterers (e.g., illustrative blood cell 309) in the portion of subsurface vasculature 307 and the detection of a flow property of the blood due to time-dependent changes in the detected pattern of constructive and destructive interference in the scattered light emitted by the tissue of the arm 305 is intended as a non-limiting illustrative example of the detection of flow properties of environments that scatter light and that include scatterers that have time-dependent properties (e.g., location, orientation) related to flow in the environment. For example, the environment could be any tissue of a human (e.g., an ankle, an ear, a neck, a portion of central vasculature) or animal, and the flow property could be a property of flow in any fluid of the human or animal body (e.g., arterial blood, capillary blood, venous blood, lymph, interstitial fluid, stomach or other digestive contents, air in the airways and/or lungs, cerebrospinal fluid). The environment could be an in vivo biological environment (e.g., a tissue of a living human, animal, plant, etc.) or an in vitro environment. The environment could be a biological sample in a sample container, cuvette, pipette, microscope slide, or other vessel. The environment could be part of a biological or chemical process. For example, the environment could be a fluid in a water treatment process, a fluid in a food or drug preparation process, a lake, stream, or river in a natural environment, a, or some other environment. The environment could be a liquid, a gel, a solid, or some other phase of matter or combination of phases (e.g., an emulsion). The environment could include biological samples that had been freeze-dried, desiccated, frozen, vaporized, alkalated, or otherwise prepared, including adding the imaging agent (i.e., functionalized nanodiamonds and functionalized magnetic particles) to the environment.

Scatterers in the environment could be discrete particles (e.g., blood cells, other cells, micelles, vacuoles, immiscible globules (e.g., oil globules in water), engineered particles (e.g., quantum dots, PEG particles, microparticles of a conductive, semiconductive, magnetic, or other material)) in the environment, or could be discontinuities within the fluid whose flow is being determined (e.g., cavitation bubbles, localized turbulence, high thermal and/or pressure gradients, shock waves). The scatterers could be present in the environment (e.g., cells in blood or other biological fluids, microorganisms, particles of silt, or other scatterers in an environmental fluid (e.g., a stream, a pond)) or could be introduced (e.g., production of cavitation bubbles by application of directed energy and/or mechanical intervention, injection of scattering particles (e.g., functionalized particles) into the bloodstream of a human or animal).

Scatterers in an environment could have one or more properties that can be detected and that are related to one or more properties of the environment. For example, a scatterer could selectively interact with an analyte of interest (e.g., the scatterer could be functionalized with a bioreceptor specific to the analyte) and a drag coefficient or other property of the scatterer could be related to the scatterer binding to the analyte. Thus, detection of the velocity of such an individual scatterer or population of such scatterers, relative to one or more determined and/or detected flow properties of the environment containing the scatterer(s), could enable determination of one or more properties of the analyte (e.g., a concentration of the analyte).

Those of skill in the art will understand the term "scatterer" in its broadest sense and that it may take the form of any natural or fabricated material, a cell, a protein or aggregate of proteins, a molecule, cryptophan, a virus, a micelle, a phage, a nanodiamond, a nanorod, a quantum dot, a single-magnetic-domain crystal of a metal, etc. that can interact with light incident on the scatterer to reflect, refract, diffract, or otherwise scatter the incident light. Scatterers could be naturally present in an environment of interest (e.g., blood cells in a portion of subsurface vasculature) or could be added to the environment of interest. Further, a scatterer may be of any shape, for example, spheres, rods, non-symmetrical shapes, etc., and may be made of a solid, liquid or gaseous material or combinations thereof.

III. Example Devices

Figure 4:
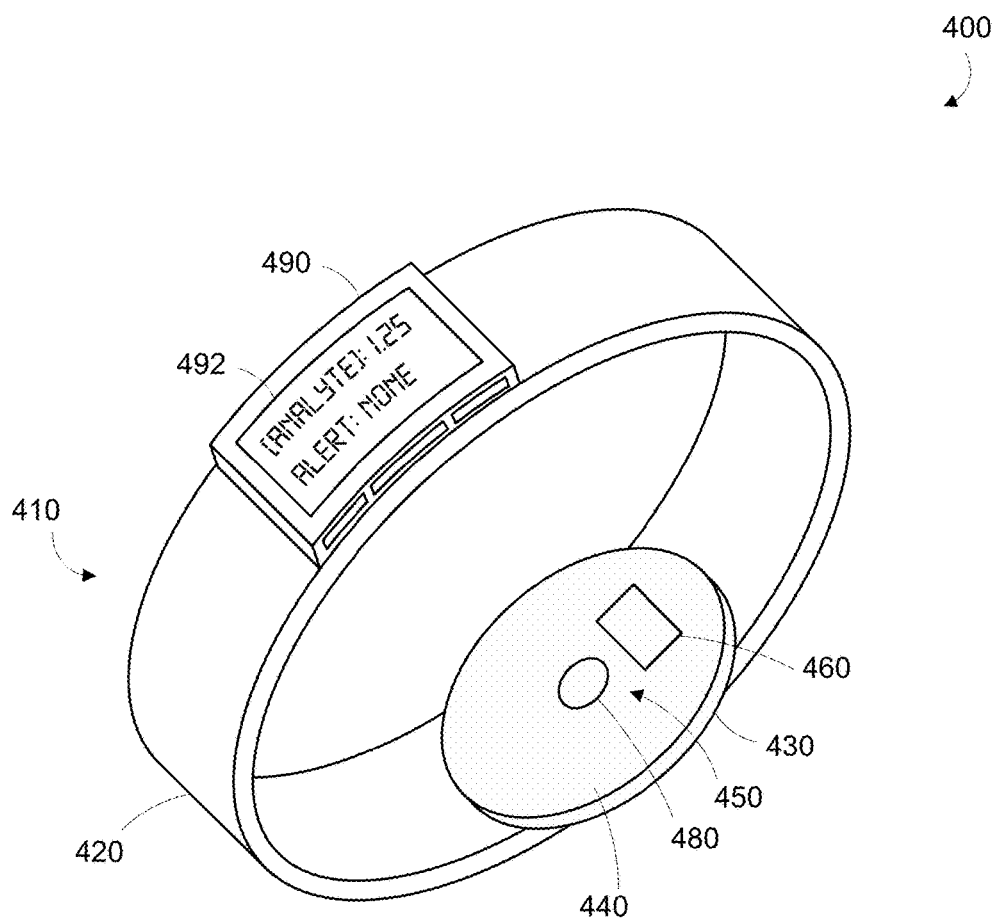
FIG. 4 is a perspective view of an example wearable device.

A wearable device 400 (illustrated in FIG. 4) can automatically measure a flow property of blood in a portion of subsurface vasculature of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 410, such as a belt, wristband, ankle band, etc. can be provided to mount the device at, on or in proximity to the body surface. The mount 410 may prevent the wearable device from moving relative to the body to reduce measurement error and noise. In one example, shown in FIG. 4, the mount 410, may take the form of a strap or band 420 that can be worn around a part of the body. Further, the mount 410 may be an adhesive substrate for adhering the wearable device 400 to the body of a wearer.

A measurement platform 430 is disposed on the mount 410 such that it can be positioned on the body where subsurface vasculature is easily observable. An inner face 440 of the measurement platform is intended to be mounted facing to the body surface. The measurement platform 430 may house a data collection system 450, which may include at least one laser 480 configured to emit a beam of coherent illumination into a portion of subsurface vasculature. The measurement platform 430 additionally includes at least one light sensor 460 configured to detect a pattern of constructive and destructive interference in light emitted from the portion of subsurface vasculature in response to illumination from the laser 480. In a non-exhaustive list, the light sensor 460 may include one or more of a photodiode, a phototransistor, a photoresistor, an active pixel sensor, a CCD, a camera, or some other light sensitive element configured to detect one or more properties of a pattern of constructive and destructive interference in the emitted light. The components of the data collection system 450 may be miniaturized so that the wearable device may be worn on the body without significantly interfering with the wearer's usual activities.

The data collection system 450 may additionally include additional detectors for detecting other physiological parameters, which could include any parameters that may relate to the health of the person wearing the wearable device. For example, the data collection system 450 could include detectors configured to measure blood pressure, pulse rate, respiration rate, skin temperature, etc. In a non-exhaustive list, additional detectors may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

The laser 480 is configured to transmit a beam of coherent illumination that can penetrate the wearer's skin into the portion of subsurface vasculature, for example, into a lumen of the subsurface vasculature. The transmitted illumination can be any kind of illumination that is benign to the wearer and that results at least in scattering of the beam of illumination to produce a pattern of constructive and destructive interference in light emitted from the portion of subsurface vasculature that is related to the disposition of scatterers (e.g., blood cells) in a flow of blood in the portion of subsurface vasculature. The wavelength of the transmitted illumination could be specified to penetrate biological tissues of a wearer; for example, the transmitted illumination could have a wavelength within a near-infrared (NIR) transparency window of biological tissue (e.g., between approximately 780 nanometers and approximately 810 nanometers). The wavelength of the transmitted illumination could be specified to be a wavelength that is scattered by blood cells. The wavelength of the transmitted illumination could be between approximately 400 nanometers and approximately 1000 nanometers.

The wearable device 400 may also include a user interface 490 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 490 may include a display 492 where a visual indication of the alert or recommendation may be displayed. The display 492 may further be configured to provide an indication of the measured physiological parameters, for instance, a determined rate of flow of blood in a portion of subsurface vasculature.

Figure 5A:
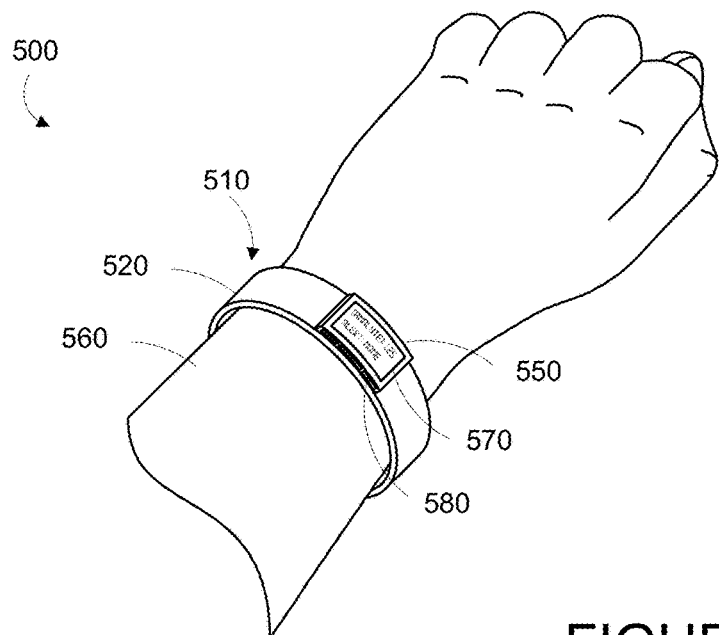
FIG. 5A is a perspective top view of an example wrist-mounted device, when mounted on a wearer's wrist.
Figure 5B:
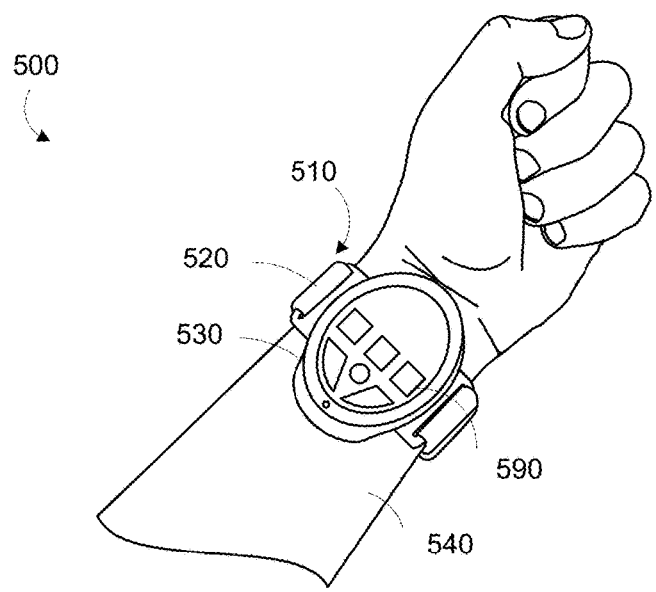
FIG. 5B is a perspective bottom view of an example wrist-mounted device shown in FIG. 5A, when mounted on a wearer's wrist.

In some examples, the wearable device is provided as a wrist-mounted device, as shown in FIGS. 5A, 5B, and 6A-6C. The wrist-mounted device may be mounted to the wrist of a living subject with a wristband or cuff, similar to a watch or bracelet. As shown in FIGS. 5A and 5B, the wrist mounted device 500 may include a mount 510 in the form of a wristband 520, a measurement platform 530 positioned on the anterior side 540 of the wearer's wrist, and a user interface 550 positioned on the posterior side 560 of the wearer's wrist. The wearer of the device may receive, via the user interface 550, one or more recommendations or alerts generated either from a remote server or other remote computing device, or alerts from the measurement platform. Such a configuration may be perceived as natural for the wearer of the device in that it is common for the posterior side 560 of the wrist to be observed, such as the act of checking a wrist-watch. Accordingly, the wearer may easily view a display 570 on the user interface. Further, the measurement platform 530 may be located on the anterior side 540 of the wearer's wrist where the subsurface vasculature may be readily observable. However, other configurations are contemplated.

The display 570 may be configured to display a visual indication of the alert or recommendation and/or an indication of the measured physiological parameters, for instance, the flow rate or other flow property of blood in a portion of subsurface vasculature of the wearer. Further, the user interface 550 may include one or more buttons 580 for accepting inputs from the wearer. For example, the buttons 580 may be configured to change the text or other information visible on the display 570. As shown in FIG. 5B, measurement platform 530 may also include one or more buttons 590 for accepting inputs from the wearer. The buttons 590 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 6A:
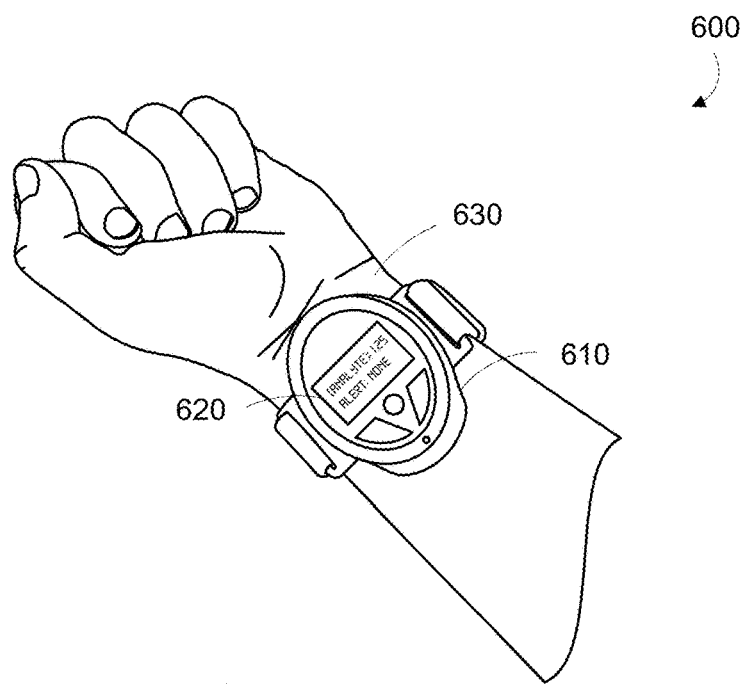
FIG. 6A is a perspective bottom view of an example wrist-mounted device, when mounted on a wearer's wrist.
Figure 6B:
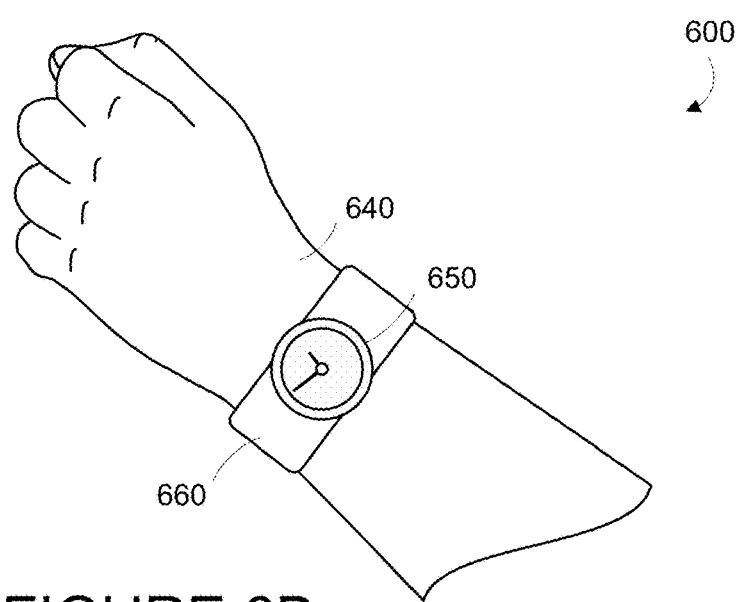
FIG. 6B is a perspective top view of an example wrist-mounted device shown in FIG. 6A, when mounted on a wearer's wrist.
Figure 6C:
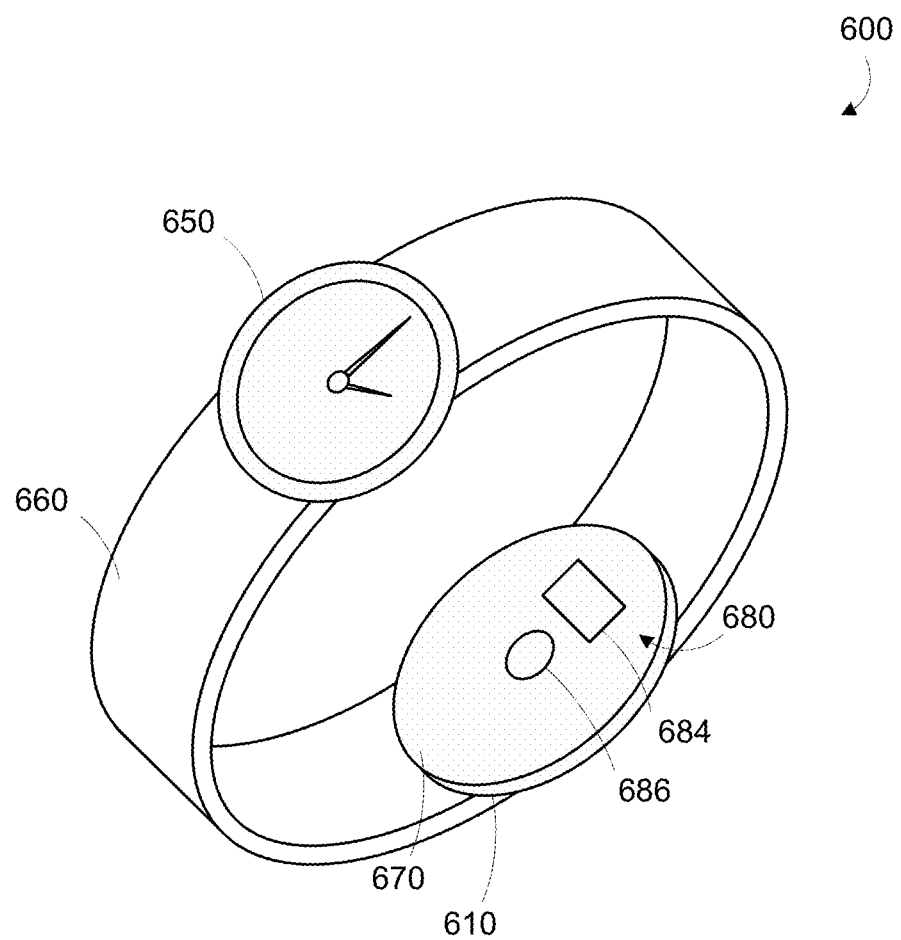
FIG. 6C is a perspective view of an example wrist-mounted device shown in FIGS. 6A and 6B.

In another example wrist-mounted device 600, shown in FIGS. 6A-6C, the measurement platform 610 and user interface 620 are both provided on the same side of the wearer's wrist, in particular, the anterior side 630 of the wrist. On the posterior side 640, a watch face 650 may be disposed on the strap 660. While an analog watch is depicted in FIG. 6B, one of ordinary skill in the art will recognize that any type of clock may be provided, such as a digital clock. As can be seen in FIG. 6C, the inner face 670 of the measurement platform 610 is intended to be worn proximate to the wearer's body. A data collection system 680 housed on the measurement platform 610 may include a laser 686 and light sensor 684.

FIG. 7 is a simplified schematic of a system including one or more wearable devices 700. The one or more wearable devices 700 may be configured to transmit data via a communication interface 710 over one or more communication networks 720 to a remote server 730. In one embodiment, the communication interface 710 includes a wireless transceiver for sending and receiving communications to and from the server 730. In further embodiments, the communication interface 710 may include any means for the transfer of data, including both wired and wireless communications. For example, the communication interface may include a universal serial bus (USB) interface or a secure digital (SD) card interface. Communication networks 720 may be any one of may be one of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 700 transmits data to a mobile phone or other personal computing device, which in turn transmits the data to the server 730.

In addition to receiving communications from the wearable device 700, such as collected physiological parameter data and data regarding health state as input by the user, the server may also be configured to gather and/or receive either from the wearable device 700 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat diabetes, but the server receives data from the wearable device indicating that the wearer's blood glucose has been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Figure 8:
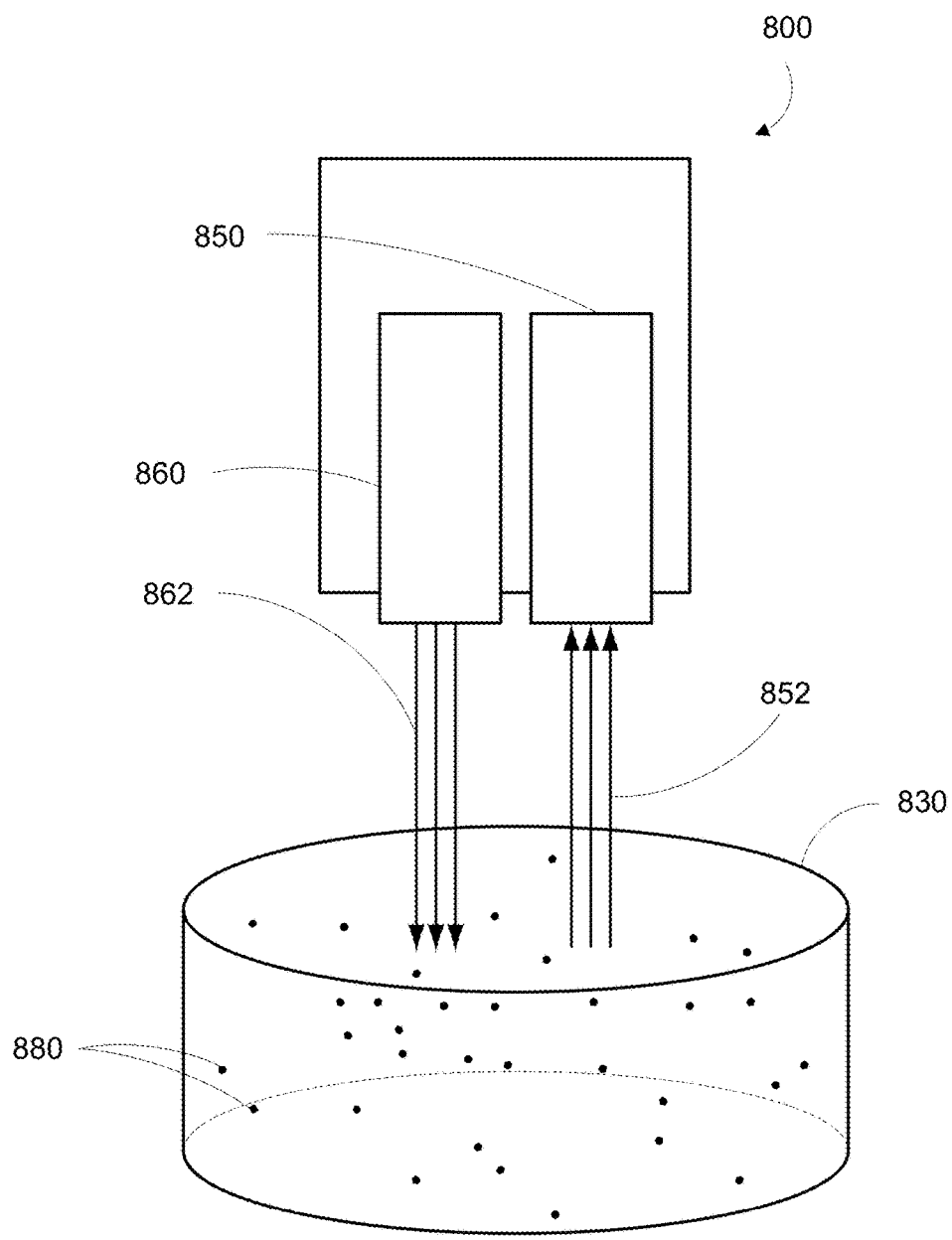
FIG. 8 is a perspective view of an example device.

A device 800 as illustrated in FIG. 8 can determine a flow property (e.g., a flow rate, a velocity of one or more particles in a fluid flow) of an environment 830 by emitting a beam of coherent illumination 862 into the environment 830 using a laser 860 and detecting a pattern of constructive and destructive interference in emitted light 852 that is emitted by the environment 830 in response to illumination using a light sensor 850. The environment 830 can be any environment containing scatterers 880 such that the scatterers 880 and other elements of the environment 830 scatter the beam of coherent light 862 in a manner that causes the pattern of constructive and destructive interference in the emitted light 852 to have one or more time-dependent properties related to a flow property of the environment 830.

The environment 830 could be an in vivo biological environment (e.g., a tissue of a living human, animal, plant, etc.) or an in vitro environment. The environment 830 could be a biological sample in a sample container, cuvette, pipette, microscope slide, or other vessel. The environment 830 could be part of a biological or chemical process. For example, the environment 830 could be a fluid in a water treatment process, a fluid in a food or drug preparation process, a lake, stream, or river in a natural environment, or some other environment. The environment 830 could be a liquid, a gel, or some other phase of matter or combination of phases (e.g., an emulsion). The environment 830 could include biological samples that had been freeze-dried, desiccated, frozen, vaporized, alkalated, or otherwise prepared, including adding natural and/or artificial scatterers 880 to the environment 830.

The light sensor 850 and laser 860 could be configured as illustrated in FIG. 8 (i.e., separate, parallel, non-coaxial) or could be configured in another way, according to an application. In some examples, the light sensor 850 and laser 860 could be coupled to a set of optical elements to enable some function. In an example, the laser 860 could include two laser light sources configured to produce beams of illumination, where the directions of the beams are controllable using some apparatus, for example a set of galvanometer-driven mirrors. The galvanometers could be operated such that flow properties in specified regions (where the beams from the laser light sources are directed) could be illuminated such a flow property of fluid flows in the specified regions could be determined. Other configurations and applications are anticipated.

IV. Example Electronics Platform for a Device

Figure 9:
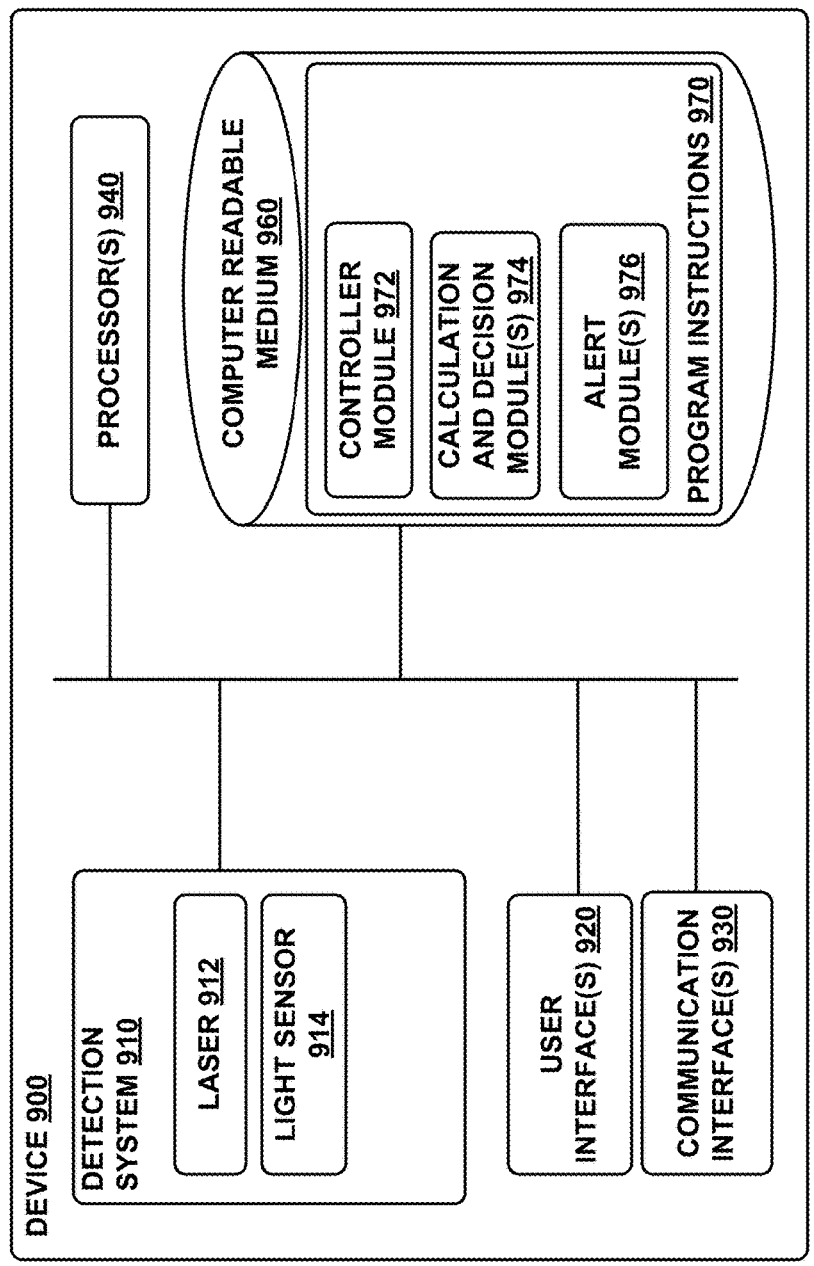
FIG. 9 is a functional block diagram of an example device.

FIG. 9 is a simplified block diagram illustrating the components of a device 900, according to an example embodiment. Device 900 may take the form of or be similar to one of the wrist-mounted devices 100, 300, 400, 500, 600 shown in FIGS. 1, 3A-C, 4, 5A-B, and 6A-6C. However, device 900 may also take other forms, such as an ankle, waist, or chest-mounted device. Device 900 could also take the form of a device that is not configured to be mounted to a body. For example, device 900 could take the form of a handheld device configured to be maintained in proximity to an environment of interest (e.g., a body part, a biological sample container, a volume of a water treatment system) by a user or operator of the device 900 or by a frame or other supporting structure. Device 900 could also take the form of a device configured to illuminate and to detect emitted light from an in vitro biological environment or some other environment, for example, a fluid volume within a water treatment process. Device 900 also could take other forms (e.g., device 800 illustrated in FIG. 8).

In particular, FIG. 9 shows an example of a wearable device 900 having a detection system 910, a user interface 920, communication interface 930 for transmitting data to a remote system, processor 940, and a computer readable medium 960. The components of the wearable device 900 may be disposed on a mount or on some other structure for mounting the device to enable stable detection of a flow property of an environment of interest, for example, to an external body surface where a portion of subsurface vasculature is readily observable.

Processor 940 may be a general-purpose processor or a special purpose processor (e.g., digital signal processors, application specific integrated circuits, etc.). The one or more processors 940 can be configured to execute computer-readable program instructions 970 that are stored in the computer readable medium 960 and that are executable to provide the functionality of a device 900 described herein.

The computer readable medium 960 may include or take the form of one or more non-transitory, computer-readable storage media that can be read or accessed by at least one processor 940. The one or more computer-readable storage media can include volatile and/or non-volatile storage components, such as optical, magnetic, organic or other memory or disc storage, which can be integrated in whole or in part with at least one of the one or more processors 940. In some embodiments, the computer readable medium 960 can be implemented using a single physical device (e.g., one optical, magnetic, organic or other memory or disc storage unit), while in other embodiments, the computer readable medium 960 can be implemented using two or more physical devices.

Detection system 910 includes a light sensor 914 and a laser 912. The laser 912 is configured to emit a beam of coherent illumination into an environment of interest. The detection system 910 additionally includes at least one light sensor 914 configured to detect a pattern of constructive and destructive interference in light emitted from the environment of interest in response to illumination from the laser 912. In a non-exhaustive list, the light sensor 914 may include one or more of a photodiode, a phototransistor, a photoresistor, an active pixel sensor, a CCD, a camera, or some other light sensitive element configured to detect one or more properties of a pattern of constructive and destructive interference in the emitted light.

The detection system 910 may additionally include additional detectors for detecting physiological parameters of a human whose body includes the environment of interest (e.g., the environment of interest is a portion of subsurface vasculature of the human), which could include any parameters that may relate to the health of the person being measured by the device 900. For example, the detection system 910 could include detectors configured to measure blood pressure, pulse rate, respiration rate, skin temperature, etc. In a non-exhaustive list, additional detectors may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

The detection system 910 could additionally include electronics configured to operate the laser 912 and the light sensor 914. The electronics could include a high-speed analog-to-digital converter (ADC) configured to sample an output (e.g., a voltage, a current) of the light sensor 914 at a specified high rate (e.g., one megahertz) to detect features of individual speckle events in the output of the light sensor 914 that have one or more properties (e.g., a pulse width, a rise time, a rise rate) related to a flow property of an environment of interest. Additionally or alternatively, the electronics could include an analog frontend that includes analog circuitry configured to filter, decimate, quantize, or otherwise alter and/or perform other analog operations or computations on the output of the light sensor 914 to produce an output electronic signal that is related to the flow property of the environment (e.g., a flow property in the portion of subsurface vasculature). This output electronic signal could then be used (e.g., sampled by an ADC of a microcontroller) to determine the flow property. In examples wherein the light sensor 914 has a plurality of electronic outputs (e.g., a plurality of voltage outputs relating to the amplitude of light detected by a plurality of light-sensitive elements) and/or wherein the device 900 includes a plurality of light sensors, the electronics could include a plurality of such analog frontends configured to receive respective outputs from respective lights sensors/elements of light sensors and to output respective electronic signals related to the respective received sensor output signals. Additionally or alternatively, the electronics could include fewer instances of such an analog frontend, and the outputs of respective light sensors could be electronically multiplexed such that the fewer instances of the analog frontend could be operated in combination with the outputs of the respective light sensors.

The program instructions 970 stored on the computer readable medium 960 may include instructions to perform any of the methods described herein. For instance, in the illustrated embodiment, program instructions 970 include a controller module 972, calculation and decision module 974 and an alert module 976.

The controller module 972 can include instructions for operating the detection system 910, for example, the laser 912 and the light sensor 914. For example, the controller module 972 may operate laser 912 and the light sensor 914 during each of a set of pre-set measurement periods. In particular, the controller module 972 can include instructions for operating the laser 912 to emit a beam of coherent illumination into a target environment (e.g., tissue of a wearer of the device 900) and controlling the light sensor 914 to detect a pattern of constructive and destructive interference in light responsively emitted by the environment being interrogated by the device 900.

The controller module 972 can also include instructions for operating a user interface 920. For example, controller module 972 may include instructions for displaying data collected by the detection system 910 and analyzed by the calculation and decision module 974, or for displaying one or more alerts generated by the alert module 976. Further, controller module 972 may include instructions to execute certain functions based on inputs accepted by the user interface 920, such as inputs accepted by one or more buttons disposed on the user interface.

Communication platform 930 may also be operated by instructions within the controller module 972, such as instructions for sending and/or receiving information via a wireless antenna, which may be disposed on or in the device 900. The communication interface 930 can optionally include one or more oscillators, mixers, frequency injectors, etc. to modulate and/or demodulate information on a carrier frequency to be transmitted and/or received by the antenna. In some examples, the device 900 is configured to indicate an output from the processor by modulating an impedance of the antenna in a manner that is perceivable by a remote server or other remote computing device.

Calculation and decision module 974 may include instructions for receiving data from and/or operating the data collection system 910, analyzing the data to determine a flow property of the environment (e.g., a flow rate of blood in a portion of subsurface vasculature), analyzing the determined flow property at one or more points in time to determine if a medical condition is indicated, or other analytical processes relating to the environment proximate to the device 900. In particular, the calculation and decision module 974 may include instructions for determining, for each preset measurement time, a flow property (e.g., a flow rate, a mean flow rate, a velocity of one or more particles in a fluid flow, a distribution of particle velocities in a fluid flow) of the environment based on one or more properties of the pattern of constructive and destructive interference detected using the light sensor 914 of the device 900. These instructions could depend on the configuration of electronic circuits of the device 900 (e.g., of the detection system 910). For example, the device 900 could include one or more ADCs configured to sample one or more outputs of the light sensor 914 at a specified high frequency, and the instructions could be executed by the processor(s) 940 to operate the one or more ADCs and to determine a flow property of the environment based on the output of the one or more ADCs. Additionally or alternatively, the device 910 could include circuitry (e.g., an analog frontend) configured to filter, modify, rectify, or otherwise perform analog operations on the one or more outputs of the light sensor 914 to produce an output electronic signal that is related to the flow property of the environment. The output electronic signal could be sampled by an ADC, comparator, or other electronic device, and the instructions could be executed by the processor(s) 940 to operate the ADC, comparator, or other electronic device to determine a flow property of the environment based on the output of the ADC, comparator, or other electronic device. These instructions could be executed at each of a set of preset measurement times.

The program instructions of the calculation and decision module 974 may, in some examples, be stored in a computer-readable medium and executed by a processor located external to the device 900. For example, the device 900 could be configured to collect certain data regarding physiological parameters from the user and then transmit the data to a remote server, which may include a mobile device, a personal computer, the cloud, or any other remote system, for further processing.

The computer readable medium 960 may further contain other data or information, such as medical and health history of a user of the device 900, that may be useful in determining whether a medical condition is indicated. Further, the computer readable medium 960 may contain data corresponding to certain blood flow profile baselines, above or below which a medical condition is indicated. The baselines may be pre-stored on the computer readable medium 960, may be transmitted from a remote source, such as a remote server, or may be generated by the calculation and decision module 974 itself. The calculation and decision module 974 may include instructions for generating individual baselines for the user of the device 900 based on data collected over a certain number of measurement periods. For example, the calculation and decision module 974 may generate a baseline blood flow profile for each of a plurality of measurement periods by averaging a blood flow profile from one or more heart beat cycles during each of the measurement periods measured over the course of a few days, and store those baseline blood flow profiles in the computer readable medium 960 for later comparison. Baselines may also be generated by a remote server and transmitted to the device 900 via communication interface 930. The calculation and decision module 974 may also, upon determining that a medical condition is indicated, generate one or more recommendations for the user of the device 900 based, at least in part, on consultation of a clinical protocol. Such recommendations may alternatively be generated by the remote server and transmitted to the device 900.

In some examples, the collected physiological parameter data, baseline blood flow profiles, health state information input by device users and generated recommendations and clinical protocols may additionally be input to a cloud network and be made available for download by a user's physician. Trend and other analyses may also be performed on the collected data, such as physiological parameter data and health state information, in the cloud computing network and be made available for download by physicians or clinicians.

Further, physiological parameter and health state data from individuals or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 974 that a medical condition is indicated, the alert module 976 may generate an alert via the user interface 920. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, seek immediate medical attention, or administer a medication.

Figure 10A:
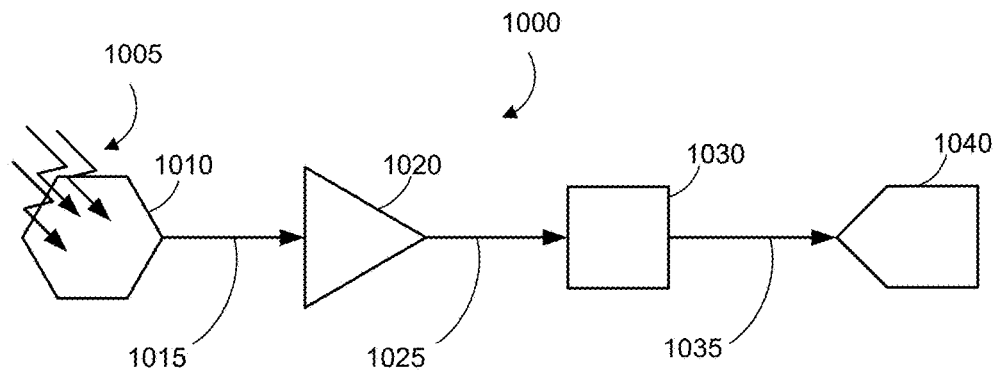
FIG. 10A is a functional block diagram of an example signal processing circuit.
Figure 10B:
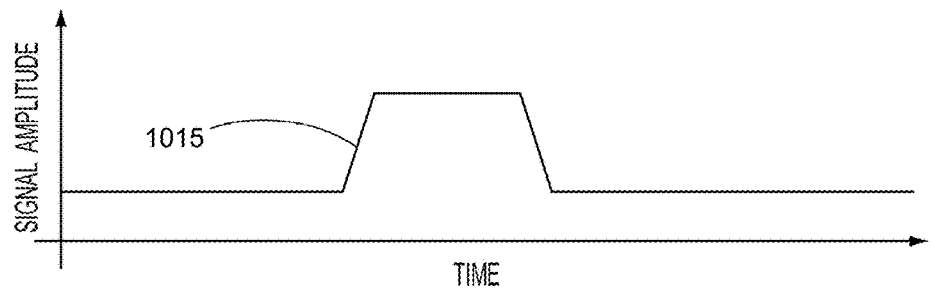
FIG. 10B is an example signal generated by the example signal processing circuit illustrated in FIG. 10A.

FIG. 10A is a functional block diagram of components that could be included in an analog frontend as described herein (e.g., an analog frontend that could be a part of the detection system 910 or of other devices described herein, e.g., 100, 300, 400, 500, 600, 800). The example analog frontend 1000 illustrated in FIG. 10A includes a light sensor 1010 configured to detect a pattern of constructive and destructive interference in emitted light 1005 that is emitted from an environment of interest (e.g., a portion of subsurface vasculature) in response to illumination by a beam of coherent light. The light sensor output 1015 is a signal related to the amplitude of the emitted light 1005 at a specified location (e.g., a location of a light-sensitive element of the light sensor 1010). FIG. 10B illustrates an example waveform of the light sensor output 1015 that includes a trapezoidal pulse corresponding to a speckle event. One or more properties of the trapezoidal pulse (e.g., a pulse width, a rise time, a rise rate, a fall time, a fall rate) could be related to a velocity of one or more scatterers in the environment of interest and/or to some other flow property of the environment of interest.

Figure 10C:
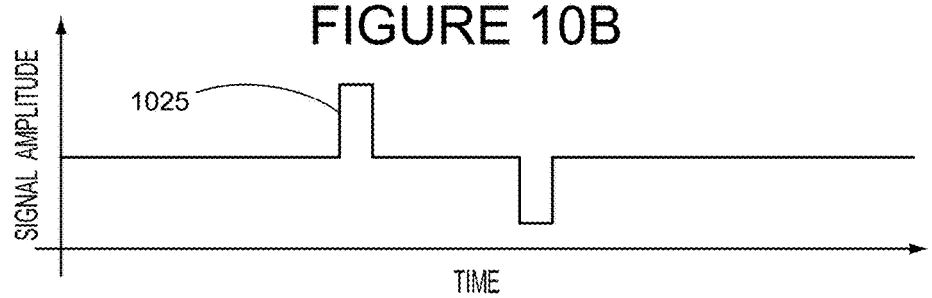
FIG. 10C is an example signal generated by the example signal processing circuit illustrated in FIG. 10A.

The example analog frontend 1000 additionally includes a differentiator 1020 configured to output a differentiator output 1025 related to a rate of change of the light sensor output 1015. The differentiator could be passive (e.g., an RC and/or RL filter circuit), active (e.g., an op-amp configured with capacitors, resistors, and/or other elements as a differentiator), or some combination thereof. Further, the differentiator output 1025 could be related to the rate of change of the light sensor output 1015; for example, the differentiator 1020 could output a low-passed, rectified, or otherwise altered version of the rate of change of the light sensor output 1015. FIG. 10C illustrates an example waveform of the differentiator output 1025 corresponding to the trapezoidal pulse in the example light sensor output 1015 waveform illustrated in FIG. 10B. The example waveform in FIG. 10C includes a first pulse having an amplitude related to a rise rate of the trapezoidal pulse illustrated in FIG. 10B and a timing corresponding to the rising edge of the trapezoidal pulse. The example waveform in FIG. 10C additionally includes a second pulse having an amplitude related to a fall rate of the trapezoidal pulse illustrated in FIG. 10B and a timing corresponding to the falling edge of the trapezoidal pulse. Note that a differentiator output 1025 waveform corresponding to the example trapezoidal pulse could have a different shape according to the configuration of the differentiator 1020. For example, the differentiator 1020 could be configured to output a signal corresponding to a rectified or otherwise filtered version of the light sensor output 1015 and the example differentiator output 1025 would be changed correspondingly (in this example, the first pulse in the example differentiator output 1025 would be filtered (e.g., would have some larger, finite rise time/fall time, etc.) and would substantially lack to second pulse).

Figure 10D:
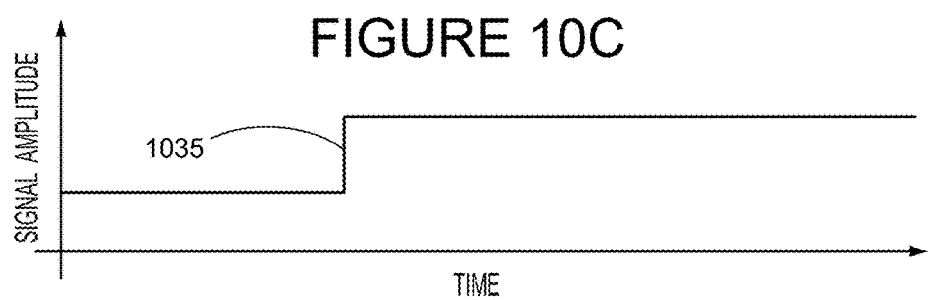
FIG. 10D is an example signal generated by the example signal processing circuit illustrated in FIG. 10A.

The example analog frontend 1000 additionally includes a peak detector 1030 configured to output a peak detector output 1035 related to a maximum value of the differentiator output 1025 during a specified previous time period. The peak detector 1030 could include passive and active components configured in a variety of ways. In some examples, the peak detector 1030 could include an op-amp, a rectifier, and a capacitor configured to output a peak detector output 1035 corresponding to a maximum value of the differentiator output 1025 in the past. The peak detector 1030 could additionally include a reset electronic switch that could be operated to reset the peak detector 1030, allowing the peak detector output 1035 to correspond to a maximum value of the differentiator output 1025 during a previous time period specified by the operation of the electronic switch. Additionally or alternatively, the peak detector 1030 could include a lossy integrator. FIG. 10D illustrates an example waveform of the peak detector output 1035 corresponding to the positive and negative pulses in the example differentiator output 1025 waveform illustrated in FIG. 10C. The example waveform in FIG. 10D includes a positive step pulse having an amplitude corresponding to the amplitude of the first pulse illustrated in FIG. 10C and a timing corresponding to the rising edge of the first pulse. Note that a peak detector output 1035 waveform corresponding to the example first and second pulses could have a different shape according to the configuration of the peak detector 1030. For example, the peak detector 1030 could include a lossy integrator, and the example peak detector output 1035 would be changed correspondingly (in this example, the step response would decay to lower signal levels over time). In another example, the peak detector 1030 could include an electronic switch operated to periodically reset the peak detector 1030, and the example peak detector output 1035 would be changed correspondingly (in this example, the step response would be replaced with a pulse having a duration corresponding to a difference in time between the timing of the first pulse of the example differentiator output 1025 and the timing of a subsequent operation of the electronic switch).

The peak detector output 1035 could form the output of the example analog frontend 1000, and could be used to determine a flow property of the environment. As illustrated in FIG. 1040, an analog-to digital (ADC) converter 1040 could be configured and operated to sample the peak detector output 1035 at one or more points in time. For example, the ADC 1040 could be operated by a microcontroller, and the microcontroller could use the output of the ADC 1040 to determine a flow property of the environment of interest (e.g., the microcontroller could determine a flow rate corresponding to an amplitude of the peak detector output 1035 measured using the ADC 1040).

V. Illustrative Methods

Figure 11:
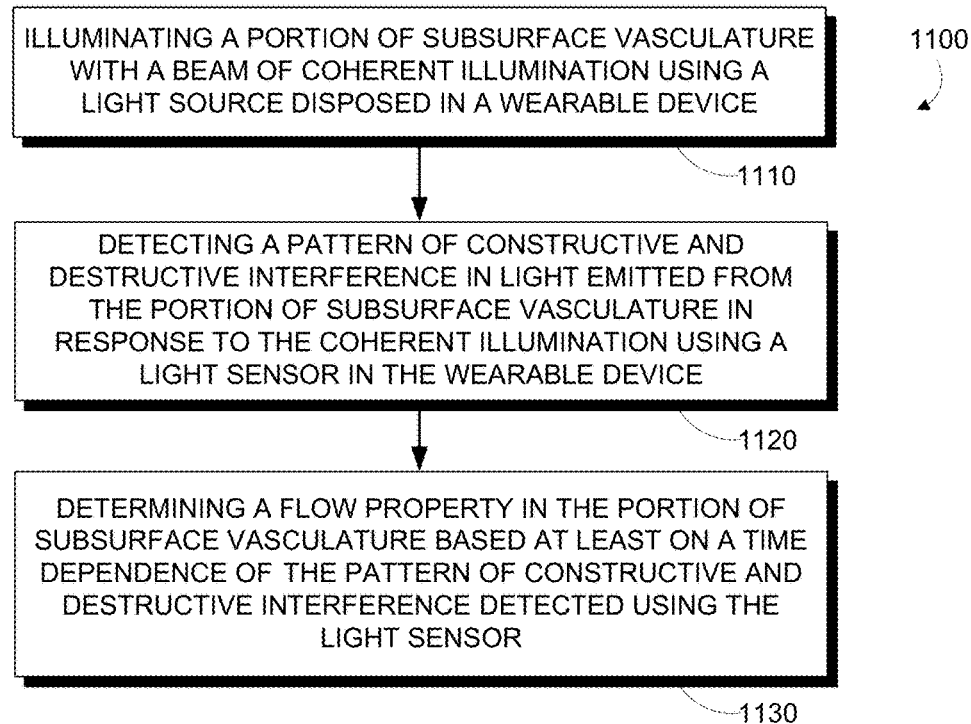
FIG. 11 is a flow chart of an example method.

FIG. 11 is a flowchart of a method 1100 for measuring a flow property in a portion of subsurface vasculature using a wearable device. The wearable device includes a light source (e.g., a laser) configured to illuminate the portion of subsurface vasculature with a beam of coherent illumination and a light sensor configured to detect a pattern of constructive and destructive interference in light emitted from the portion of subsurface vasculature in response to illumination by the light source. The wearable device could include additional elements according to an application. For example, the wearable device could include a controller, a battery, a user interface, analog electronics, or other components configured to facilitate operation of the laser and the light sensor. The wearable device could include a mount or other component configured to position the wearable device on the body of a wearer, for example a band configured to attach the wearable device around a wrist, ankle, or other part of a wearer's body where a flow property in a portion of subsurface vasculature could be detected.

The method 1100 includes illuminating the portion of subsurface vasculature with a beam of coherent illumination using the light source 1110. The coherent illumination is such that scatterers and other elements in the environment scatter the coherent illumination such that light is responsively emitted from the environment having a pattern of constructive and destructive interference that is related at least to the configuration of the scatterers in the fluid flow. As such, the pattern of constructive and destructive interference could have a time-dependence related to a flow property of the environment (e.g., a flow rate of the fluid flow). This can include emitting coherent illumination having a specific wavelength or coherence length, such that the coherent illumination can be scattered by scatterers disposed in a fluid flow in the environment, efficiently transmitted through the environment, or other considerations. Exposing the environment to coherent illumination 1110 can include emitting coherent illumination having a specified amplitude, wavelength, coherence length, spectral line width, polarization, or other property. Further, exposing the environment to coherent illumination 1110 can include emitting coherent illumination having different properties at different points in time. For example, it could include emitting coherent illumination having a first amplitude, wavelength, coherence length, spectral line width, polarization, or other property at a first point in time and emitting coherent illumination having a second amplitude, wavelength, coherence length, spectral line width, polarization, or other property at a second point in time.

The method 1100 additionally includes detecting a pattern of constructive and destructive interference in light emitted from the portion of subsurface vasculature in response to the coherent illumination using the light sensor 1120. This can include detecting the amplitude, wavelength, degree of polarization, orientation of polarization, or other properties of the emitted light at a point on or within the wearable device (e.g., a sensitive area of a photodetector, an aperture of a camera). It can also include detecting one or more properties of light emitted from the portion of subsurface vasculature at more than one point. For example, the light sensor could include a plurality of light sensitive elements (e.g., photodiodes, phototransistors, active pixel sensors, pixels of a CCD) disposed in an array or other arrangement on a surface of the wearable device.

The method 1100 additionally includes determining a flow property in the portion of subsurface vasculature based at least on a time dependence of the pattern of constructive and destructive interference detected using the light sensor 1130. This could include determining a flow rate of blood in the portion of subsurface vasculature, a mean flow rate of blood in the portion of subsurface vasculature, a flow profile of blood at different locations in the portion of subsurface vasculature, a velocity of one or more scatterers or other elements in blood in the portion of subsurface vasculature, a distribution of velocities of scatterers or other elements in blood in the portion of subsurface vasculature, or some other flow property or properties in the portion of subsurface vasculature.

Determining a flow property in the portion of subsurface vasculature 1130 could include sampling an output of the light sensor (e.g., an output related to an intensity of light, a local or overall contrast of the pattern of subsurface vasculature, or some other property or properties of the detected pattern of constructive and destructive interference) at a high frequency and then performing some calculation on the sampled output (e.g., determining a rate of amplitude change, a number of speckle events, a temporal property (e.g., duration, rise time) of speckle events) to determine the flow property. Additionally or alternatively, electronics (e.g., an analog frontend) of the wearable device could be configured to filter, modify, rectify, or otherwise perform analog operations on an output of the light sensor to produce an output electronic signal that is related to the flow property of the environment. Determining a flow property in the portion of subsurface vasculature 1130 could include sampling the output electronic signal and then performing some calculation on the sampled output electronic signal to determine the flow property. Additional or alternative embodiments and/or steps of determining a flow property in the portion of subsurface vasculature 1130 are anticipated.

The method 1100 could include additional steps or elements in addition to exposing the environment to coherent illumination 1110, detecting a pattern of constructive and destructive interference 1120, and determining a flow property in the portion of subsurface vasculature 1130. For example, the method 1100 could include mounting the wearable device to an external body surface of the wearer proximate to the portion of subsurface vasculature. The method could include indicating a determined flow property to a user using a user interface of the device or to some other person or system(s) by some other means (e.g., a wireless communications component of the wearable device). The method 1100 could include introducing scatterers into the environment (e.g., injecting, ingesting, transdermally transferring, or otherwise introducing the scatterers into a lumen of vasculature of a human).

The method 1100 could include determining some other information about a wearer based on one or more determined flow properties (e.g., flow rates of blood) in the portion of subsurface vasculature during one or more periods of time. For example, a determined flow rate or other flow property of blood in the portion of subsurface vasculature determined at one or more points in time could be used to determine a blood pressure in the portion of subsurface vasculature. One or more determined flow properties in the portion of subsurface vasculature could be used to determine a health state of the wearer. For example, a plurality of flow rates of blood determined at a respective plurality of points in time could be used to determine a heart rate of the user that could further be used to determine a health state of the wearer (e.g., tachycardia, bradycardia, sleep apnea, irregular heartbeat). Additionally or alternatively, a plurality of flow rates of blood could be used to determine a flow and/or pressure profile of the blood that could further be used to determine a health state of the wearer (e.g., hypertension, aortic regurgitation). Other additional steps of the method 1100 are anticipated.

CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to detect one or more flow properties of blood in portions of subsurface vasculature of a human body, it is noted that the disclosed devices, systems, and methods can be applied in other contexts as well. For example, detection systems configured to detect one or more flow properties of fluid using laser and light sensors as disclosed herein may be included in wearable (e.g., body-mountable) and/or implantable devices. In some contexts, such a detection system is situated to be substantially encapsulated by bio-compatible polymeric material suitable for being in contact with bodily fluids and/or for being implanted. In one example, an implantable medical device that includes such a detection system may be encapsulated in biocompatible material and implanted within a host organism. Such body-mounted and/or implanted detection systems can include circuitry configured to operate lasers, light emitters, light sensors, or other elements to enable detection of flow properties of a target fluid by detecting changes over time in a speckle pattern of light scattered and/or otherwise emitted by the target fluid. The detection system can also include a communication system for wirelessly indicating detected and/or determined flow properties of a target fluid.

In other examples, devices, systems, and methods disclosed herein may be applied to measure flow properties of one or more fluids that are not in or on a human body. For example, detection systems disclosed herein may be included in body-mountable and/or implantable devices used to measure flow properties in a fluid of an animal. In another example, devices, systems, and methods disclosed herein may be applied to measure flow properties of an environmental fluid, such as a fluid in a river, lake, marsh, reservoir, water supply, sanitary sewer system, storm sewer system, or the atmosphere. In another example, devices, systems, and methods disclosed herein may be applied to measure flow properties of a fluid that is part of a process, such as a waste treatment process, industrial process, pharmaceutical synthesis process, food preparation process, fermentation process, or medical treatment process Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A device comprising:
  a light source, wherein the light source is configured to emit a beam of coherent illumination into a portion of subsurface vasculature;
  a volume holographic grating optically coupled to the light source, wherein the volume holographic grating is configured to increase a coherence length of the beam of coherent illumination emitted by the light source;
  a light sensor, wherein the light sensor detects a pattern of constructive and destructive interference in light emitted from the portion of subsurface vasculature in response to the coherent illumination from the light source and outputs a detected light intensity waveform comprising a plurality of pulses corresponding to speckle events caused by motion of one or more individual particles in the subsurface vasculature, wherein each pulse in the plurality of pulses includes a respective rising edge, plateau, and falling edge; and
  a controller coupled to the light source and the light sensor, wherein the controller comprises an analog frontend that processes the output of the light sensor, wherein the analog frontend comprises a differentiator configured to output a signal indicative of a rate of increase during a rising edge of each respective pulse, and wherein the controller (i) determines velocities of the one or more individual particles based on the output of the differentiator, and (ii) determines a flow property of fluid in the portion of subsurface vasculature based on the determined velocities of the one or more individual particles.

2. The device of claim 1, further comprising a mount configured to mount the light source and the light sensor to an external body surface.

3. The device of claim 2, wherein the external body surface is a wrist location.

4. The device of claim 1, wherein the flow property of fluid is a flow rate of blood in the portion of subsurface vasculature.

5. The device of claim 4, wherein the beam of illumination emitted by the light source has a specified wavelength, wherein the specified wavelength is between approximately 400 nanometers and approximately 1000 nanometers.

6. The device of claim 1, further comprising an annular filter, wherein the light sensor has a specified axis, wherein the annular filter is configured to substantially block light from being received by the light sensor unless the light approaches the light sensor from an angle relative to the specified axis of the light sensor, wherein the angle has a value within a specified range of values.

7. The device of claim 1, further comprising a user interface configured to provide a user-discernible indication of the determined flow property.

8. The device of claim 1, further comprising a wireless communication interface configured to transmit data indicative of the determined flow property.

9. The device of claim 1, wherein the beam of coherent illumination emitted by the light source has a first specified wavelength, and further comprising a second light source, wherein the second light source is configured to emit a second beam of coherent illumination to illuminate the portion of subsurface vasculature, wherein the second beam of coherent illumination emitted by the second light source has a second specified wavelength that is different from the first specified wavelength.

10. The device of claim 1, wherein the controller further comprises an analog-to-digital converter.

11. The device of claim 1, further comprising:
an array of light sources, wherein individual light sources of the array of light sources are configured to emit respective beams of coherent illumination, wherein the light sources of the array of light sources are spatially distributed such that individual beams of coherent illumination emitted by respective light sources of the array of light sources illuminate respective portions of tissue, wherein the light sensor is further configured to detect respective patterns of constructive and destructive interference in light emitted from the respective portions of tissue in response to the coherent illumination from respective light sources of the array of light sources, and wherein the controller operates individual light sources of the array of light sources to illuminate respective portion of tissue and determines respective flow properties of fluid in the respective portions of tissue illuminated by the operated individual light sources.

12. The device of claim 1, wherein the individual particles are blood cells.

* * * * *